US00RE38189E

(19) United States
(12) Reissued Patent
Walker et al.

(10) Patent Number: US RE38,189 E
(45) Date of Reissued Patent: Jul. 15, 2003

(54) MEDICATION DELIVERY AND MONITORING SYSTEM AND METHODS

(75) Inventors: Richard Bradley Walker, Marietta, GA (US); Robert F. Evans, Mobile, AL (US); Robert Hanson, Mobile, AL (US); Michael F. Burrow, Grayson, GA (US)

(73) Assignee: DocuSys, Inc., Mobile, AL (US)

(21) Appl. No.: 09/362,839

(22) Filed: Jul. 28, 1999

Related U.S. Patent Documents

Reissue of:
(64) Patent No.: 5,651,775
Issued: Jul. 29, 1997
Appl. No.: 08/501,362
Filed: Jul. 12, 1995

(51) Int. Cl.[7] ..... A61M 1/00
(52) U.S. Cl. ..... 604/207
(58) Field of Search ..... 604/30–34, 506, 604/507, 511, 65, 66, 67, 154, 200–207, 411, 415; 128/DIG. 12, DIG. 13

(56) References Cited

U.S. PATENT DOCUMENTS

| | | | |
|---|---|---|---|
| 2,427,552 | A | 9/1947 | De Lancey |
| 3,152,723 | A | 10/1964 | Perl et al. |
| 3,270,548 | A | 9/1966 | Marbach |
| 3,599,833 | A | 8/1971 | Reichenberger |
| 3,656,138 | A | 4/1972 | Hamma |
| 3,677,092 | A | 7/1972 | Guarino |
| 3,677,448 | A | 7/1972 | Harris, Sr. et al. |
| 4,013,194 | A | 3/1977 | Moscarini |
| 4,074,356 | A | 2/1978 | Schiller et al. |
| 4,079,736 | A | 3/1978 | Lundquist |
| 4,105,138 | A | 8/1978 | Lehmann et al. |
| 4,121,584 | A | 10/1978 | Turner et al. |
| 4,191,184 | A | 3/1980 | Carlisle |
| 4,217,993 | A | 8/1980 | Jess et al. |
| 4,291,693 | A | 9/1981 | Todd et al. |
| 4,383,252 | A | 5/1983 | Purcell et al. |
| 4,427,132 | A | 1/1984 | Thomson |
| 4,436,223 | A | 3/1984 | Wilson |
| 4,507,604 | A | 3/1985 | Sherer |
| 4,555,940 | A | 12/1985 | Renger |
| 4,559,044 | A | 12/1985 | Robinson et al. |
| 4,562,842 | A | 1/1986 | Morfeld et al. |
| 4,589,872 | A | 5/1986 | Bellin et al. |
| 4,592,747 | A | 6/1986 | Pool |
| 4,597,507 | A | 7/1986 | Rosenblum et al. |
| 4,613,325 | A | 9/1986 | Abrams |
| 4,627,840 | A | 12/1986 | Cuadra et al. |
| 4,648,869 | A | 3/1987 | Bobo, Jr. |
| 4,650,458 | A | 3/1987 | Dahlberg et al. |

(List continued on next page.)

*Primary Examiner*—Manuel Mendez
(74) *Attorney, Agent, or Firm*—Lerner, David, Littenberg, Krumholz & Mentlik, LLP

(57) ABSTRACT

A medication delivery and monitoring system and methods whereby drugs are safely delivered to a patient, monitored in real-time during delivery and crucial events are recorded during delivery to provide real-time, on-line information and detail for an audit trail. A novel safety label cradle unit is disclosed. Safety label cradles (SLC's) are provided in a plurality of sizes to match varying sizes of syringes which are disposed on a cradle of the SLC to provide a constant needle height on the SLC unit independent of syringe volume (barrel diameter). A selected SLC is securely affixed to a syringe by an adhesively backed label wrapping. The label is preprinted to provide drug identification indicia and drug preparation information. The information is automatically read into the system from the label. A novel delivery station of the system monitors drug delivery as a plunger of the syringe is pushed to deliver a drug to a patient. A smart tray in cooperation with a slider portion of the SLC is used to selectively deliver drugs to a port in the IV set. The smart tray comprises a first portion for carrying SLC units, an attachable second portion having a control panel for operating the system and a cover for lockably affixing the SLC units to the tray.

57 Claims, 13 Drawing Sheets

U.S. PATENT DOCUMENTS 4,699,617 A 10/1987 Moriuchi et al.
4,720,636 A 1/1988 Benner, Jr.
4,736,871 A 4/1988 Luciani et al.
4,744,955 A 5/1988 Shapiro ..... 422/100
4,760,939 A 8/1988 Ball et al.
4,781,696 A 11/1988 Moulding, Jr. et al. ..... 604/189
4,784,648 A 11/1988 Singh et al.
4,802,506 A 2/1989 Aslanian
4,842,028 A 6/1989 Kaufman et al.
4,853,521 A 8/1989 Claeys et al.
4,938,072 A 7/1990 Brown et al.
4,976,687 A 12/1990 Martin
4,978,335 A 12/1990 Arthur, III ..... 604/67
5,133,480 A 7/1992 Matsumoto et al.
5,222,027 A 6/1993 Williams et al.
5,295,976 A 3/1994 Harris ..... 604/211
5,308,341 A 5/1994 Chanoch ..... 604/208
5,328,486 A 7/1994 Woodruff
5,366,454 A 11/1994 Currie et al.
5,385,559 A 1/1995 Mannix
5,433,342 A 7/1995 Luro
5,445,621 A 8/1995 Poli et al.
5,449,344 A 9/1995 Taylor et al.
5,454,793 A 10/1995 Levander et al.
5,468,233 A 11/1995 Schraga
5,522,805 A 6/1996 Vancaillie et al.
5,533,981 A 7/1996 Mandro et al. ..... 604/208
5,536,945 A * 7/1996 Reich ..... 250/507.1
5,569,212 A 10/1996 Brown
5,593,390 A 1/1997 Castellano et al. ..... 604/187
5,602,745 A 2/1997 Atchley et al.
5,609,576 A 3/1997 Voss et al.
5,632,411 A 5/1997 Harty et al.
5,662,612 A 9/1997 Niehoff ..... 604/155
5,674,204 A 10/1997 Chanoch
5,690,618 A 11/1997 Smith et al.
5,697,916 A 12/1997 Schraga ..... 604/201
5,709,670 A 1/1998 Vancaillie et al.
5,716,345 A 2/1998 Halbich
5,755,358 A 5/1998 Fisk
5,872,814 A 2/1999 McMeekin
5,882,338 A 3/1999 Gray ..... 604/131
5,925,021 A 7/1999 Castellano et al. ..... 604/207
5,928,197 A 7/1999 Niehoff ..... 604/155
5,997,502 A 12/1999 Reilly et al. ..... 604/67
6,090,064 A 7/2000 Reilly et al. ..... 604/49

* cited by examiner

Figure 6A
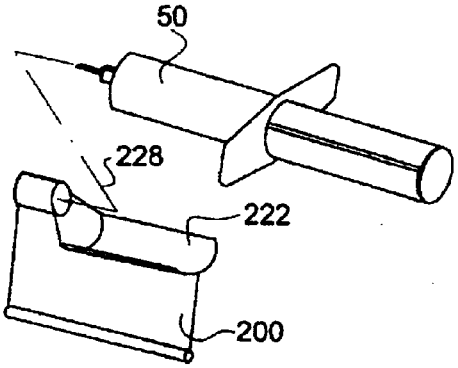
Figure 6B
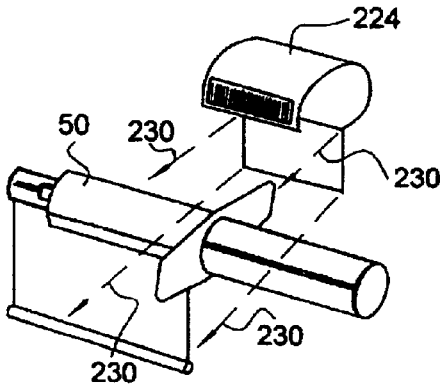
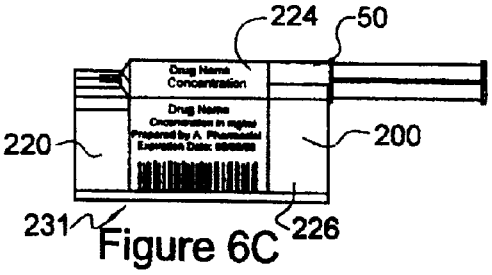
Figure 6C
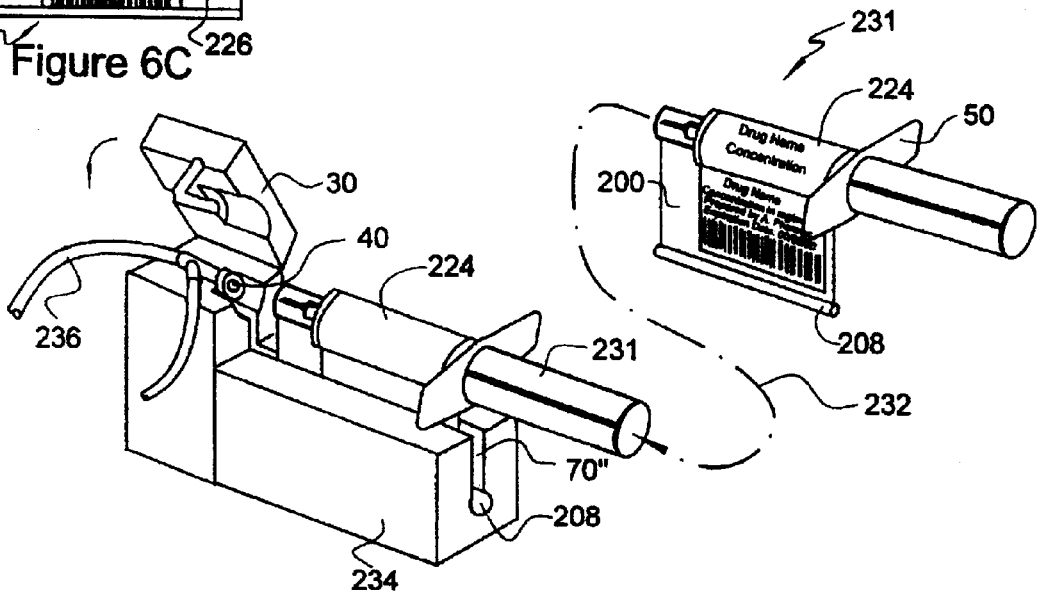
Figure 6D

MEDICATION DELIVERY AND MONITORING SYSTEM AND METHODS

Matter enclosed in heavy brackets [ ] appears in the original patent but forms no part of this reissue specification; matter printed in italics indicates the additions made by reissue.

FIELD OF INVENTION

The field of the invention is control and monitoring of medications delivered to a patient and more particularly to methods and apparatus involved in automatically controlling drug delivery, including controlling of drug administration rate and volume, with real-time monitoring and record keeping.

BACKGROUND

Problems related to misidentification and resulting erroneous delivery of drugs are well known in the medical care art. Other problems related to drug control, maintaining adequate drug records, contamination of drugs prepared on patient floors are also well known in the pharmaceutical art. This invention provides solutions to the above disclosed problems and many others as will become evident hereafter.

Manual dispensing of drugs from pharmacy to anesthesia is a common practice in hospitals and other surgery facilities today. Anesthesia providing departments generally fill syringes with drugs, administer the drugs directly to patients and document the drug handling process in a retrospective manner using handwritten entries. The likelihood of human imperfections makes drug diversion, medication errors, errors of omission, medication contamination and inadvertent needle sticks a constant companion to drug administration. Additionally, the process is exacerbated by emergency situations which demand hurried set up and administration of drugs, with concurrently less time to pay attention to timely and accurate record keeping.

Contemporarily, the problems related above are being addressed by approaches meant to improve drug delivery and control. These approaches comprise production and use of pre-packaged drug menus which involve return to the pharmacy of each unused package to simplify and assure better control in drug accounting; making drug dispensing machines which automatically dispense drugs and provide a record certain as drugs are removed therefrom; delivering drug "lock boxes" to a requesting physician, thereby putting direct responsibility for drug accounting upon the physician of record; and utilizing electronic recording devices whereby documentation of drug delivery data is captured via electronic data acquisition devices, such as bar code readers or keyboards. All of these approaches, used alone or in combination, exhibit deficiencies which are well known in the drug dispensing and monitoring art.

BRIEF SUMMARY AND OBJECTS OF THE INVENTION

In brief summary, this novel invention alleviates all of the known problems related to drug administration. The present invention pertains to a system which is used to assure proper identification and administration of prescribed drugs, to control access to drugs and to record drug distribution activities. The invention also permits direct use of centralized pharmaceutical resources in preparing medications in clean (e.g. air hood) environments where contamination is less likely, in producing standardized labeling and in packaging drugs for distribution within a medical facility. The invention is particularly well adapted for use in handling prescription dose quantities rather than single-dose medication(s), thereby providing opportunity for reduced cost of drug handling.

The present invention improves drug delivery and control by capturing all related data immediately upon administration of a drug through employment of an inventive automatic drug infusion monitoring system. Elemental parts of the system comprise a scanning module, a syringe label cradle, a cassette tray and a receptacle.

The scanning module employs bar code or other digital indicia scanners to read labels affixed to the syringe label cradle. Information contained on the label comprises a code identifying a drug contained in an associated syringe, size of the syringe, syringe type, preparer of the drug, and any expiration data associated with the drug. The scanning module readers are also used to monitor syringe plunger movement as a drug is administered thus acquiring drug administration dynamics in real time. Scanning by the scanning module may comprise two scanners, one for reading drug related codes and one for tracking advancement of an associated syringe plunger, thereby determining delivery rate and volume of administered drugs.

Dynamic control and delivery of drugs permits use of pre-filled syringes at the pharmacy and eliminates the need for unit dose sized medicants and the need for filling syringes by a bedside clinician. This approach yields cost efficiencies in both drug handling and clinician time. Prefilling syringes by batch processing under sterile hoods reduces errors and nosocomial infections and allows quick and efficient response to clinical (emergency) situations.

The syringe label cradle is a holder and positioner for a drug containing syringe. A syringe disposed in the cradle is preferably securely affixed thereto by an self-adhesing, pre-printed label. Presently preferable machine readable codes are bar codes. The syringe label cradle is instrumental in holding and positioning the syringe for drug administration as well as providing access to the label.

The cassette tray secures syringe containing syringe label cradles in place for transport and storage prior to, during and after use. The cassette tray has a lock which remains locked by the system until opened by an authorized (properly identified) clinician. Generally, the cassette tray is organized to hold syringe label cradles and their contents in a logically progressive array. In use, the cassette tray is aligned with an injection port most commonly connected to a patient-connected needleless IV injection set. In any event, a clinician advances the aligned syringe label cradle to a docked position for drug infusion after which infusion is automatically monitored and recorded.

The receptacle comprises the injection port, generally referenced hereafter as an injection port module (IPM). The receptacle also comprises a scanner module, hard copy generator (printer) and a control module. The IPM secures an IV line in position to accept selected syringe label cradles for drug injection through the port.

The scanner module reads data encoded on the label, secures the syringe label cradle in position for injection and tracks syringe plunger advancement. The printer is used to generate printouts of drug administration event chronology and other critical data either as they are recorded or after they have been stored for later printout.

The control module holds syringes containing controlled drugs (such as a narcotic syringe) in an off-use holding site. The control module continuously monitors the syringes while they remain in the holding position, thereby preventing drug diversion or other undesirable manipulations of narcotics or other control substances. Information transfer to a user is upgraded and enhanced by on-line printers and liquid crystal displays (LCD's) available on the control module. Also a real-time interface is available for transmitting and receiving electronic medical records, billings, or other standard depositories of hospital information. Further the real-time interface makes customized data bases such as pre-operative interview results, potential drug interactions, allergic reactions, physician profiling, outcome analysis available to a user at the control module.

A natural benefit of the instant invention is production of an drug administration audit trail. As well, drug access is severely limited by locked, secured lids on cassette trays. The cassette trays assuredly thereby contain only original syringes and associated syringe label cradle's (SLC's) permitting an accurate quality assurance to be maintained by pharmacy. Return of unused drugs under controlled conditions allows a significant reduction in drug waste due to otherwise unwarranted disposition.

Automatically powered needle injection into IV set injection sites under protective cover provided by a shield associated with each SLC is a major factor in eliminating needle sticks which could otherwise occur. Contamination is thereby minimized as well. Additional patient protection is provided by data contained on a patient data card which is an integral part of patient data management capability of the inventive combination.

Accordingly, it is a primary object to provide a medical drug delivery and monitoring system having capability for automatically dispensing drugs to a patient, monitoring and recording drug rates and volumes in real time, and providing drug control and drug record security throughout a medical procedure.

It is a fundamental object to provide method and apparatus for safely and securely delivering drugs to a patient site for use in a controlled manner.

It is another fundamental object to provide a Syringe Label Cradle (SLC) for securing a drug containing syringe in position for use and as an integral function thereof to provide an identifying label which is automatically read to identify the syringe, its contents, preparer of the contents, critical drug data including expiration data and drug volume available in the syringe.

It is another fundamental object to provide a cassette tray which secures SLC's in place for transport and storage, prior to, during and after use in drug infusion.

It is yet another fundamental object to provide a receptacle which comprises an injection port module (IPM) through which drugs are automatically injected into an IV line from a drug containing syringe.

It is still another fundamental object to provide a scanner within the receptacle which tracks movement of each plunger of each syringe as it is driven to inject a drug into the IV line.

It is an object to provide a printer for hard copy output of data acquired by the system, including, but not limited to, drug types, administered volumes, time of administration, and pertinent patient data.

It is a further object to provide a control module which comprises a keyboard and liquid crystal display (LCD) which permits clinician access to patient and system status, warnings, event chronology and other system and patient related parameters.

It is an important object to provide a system which sequentially utilizes portions of drugs contained in syringes placed in the SLC's thereby eliminating the necessity of prepackaging drugs in predetermined quantities, such as unit doses, and of preparing syringes at a patient site by a clinician, thereby making drug preparation more efficient, less prone to contamination and error and less expensive due to higher volume preparation at a central pharmaceutical site.

These and other objects and features of the present invention will be apparent from the detailed description taken with reference to accompanying drawings.

BRIEF DESCRIPTION OF THE DRAWINGS

FIGS. 6 A, B, C and D show a sequence of steps used in preparing and disposing a syringe, SLC and label apparatus into an IV connecting receptacle.

DETAILED DESCRIPTION OF THE ILLUSTRATED EMBODIMENTS

In this description, the term proximal is used to indicate the segment of the device normally closest to the object of the sentence describing its position. The term distal refers to the other end. Reference is now made to the embodiments illustrated in FIGS. 1–16 wherein like numerals are used to designate like parts throughout.

Figure 1:
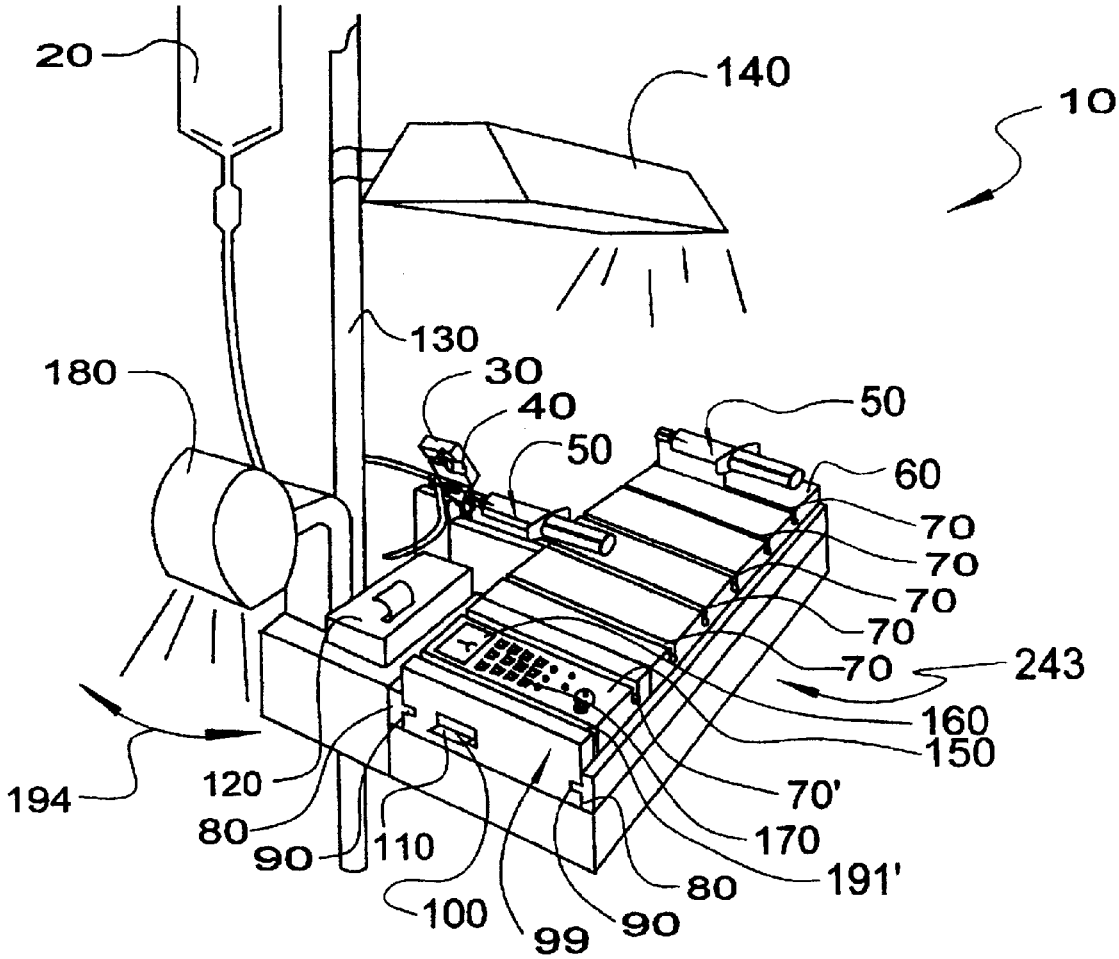
FIG. 1 is a perspective of a medication administering station.

Reference is now made to FIG. 1 wherein one embodiment of an operating room medication administration monitoring system 10 is seen. System 10 comprises an intravenous solution source 20 and an injection port module 30 comprising an injection port 40. A patient to which source 20 is ultimately connected through module 30 is not shown, but such connections to the patient are well known in the art.

System 10 also comprises a plurality of syringes 50 which reside in a tray 60. Tray 60 is commonly referenced as a smart tray due to an inherent ability of the tray to read labels and other machine readable indicia. A complete description of 60 tray operation is provided hereafter. Tray 60 comprises a scanner slot 70 for each syringe 50 position. System 10 provides a pair of transverse slide mechanisms 80 which dovetails with juxtaposed grooves 90 to permit each syringe 50 and associated slot 70 to be disposed in alignment with injection port 40.

The most proximal slot 70' is commonly dedicated to acting as a portable scanner and continuously monitors a syringe 50 placed thereat, except when the syringe 50 is advanced toward port 40 for injection or removed from slot 70'.

System 10 further comprises a scanning and recording module 99. Scanning and recording module 99 comprises a patient and procedure storage mechanism 100 for magnetically or otherwise imprinting data upon a portable data card 110 and a hard copy printer 120. Scanning and recording module 99 may be mounted upon a riser 130 upon which system 10 is securely affixed for ready and facile access and illuminated by a lamp 140. Associated with reader 100 is an operating panel 150 comprising a display (preferably a LCD) 160 and a keyboard entry pad 170 which is used for system 10 control and data entry. An optional reader 180 may be provided for scanning for entry of indicia found on supplies and other implements not otherwise recorded by system 10, but which are important to device record keeping.

Figure 2:
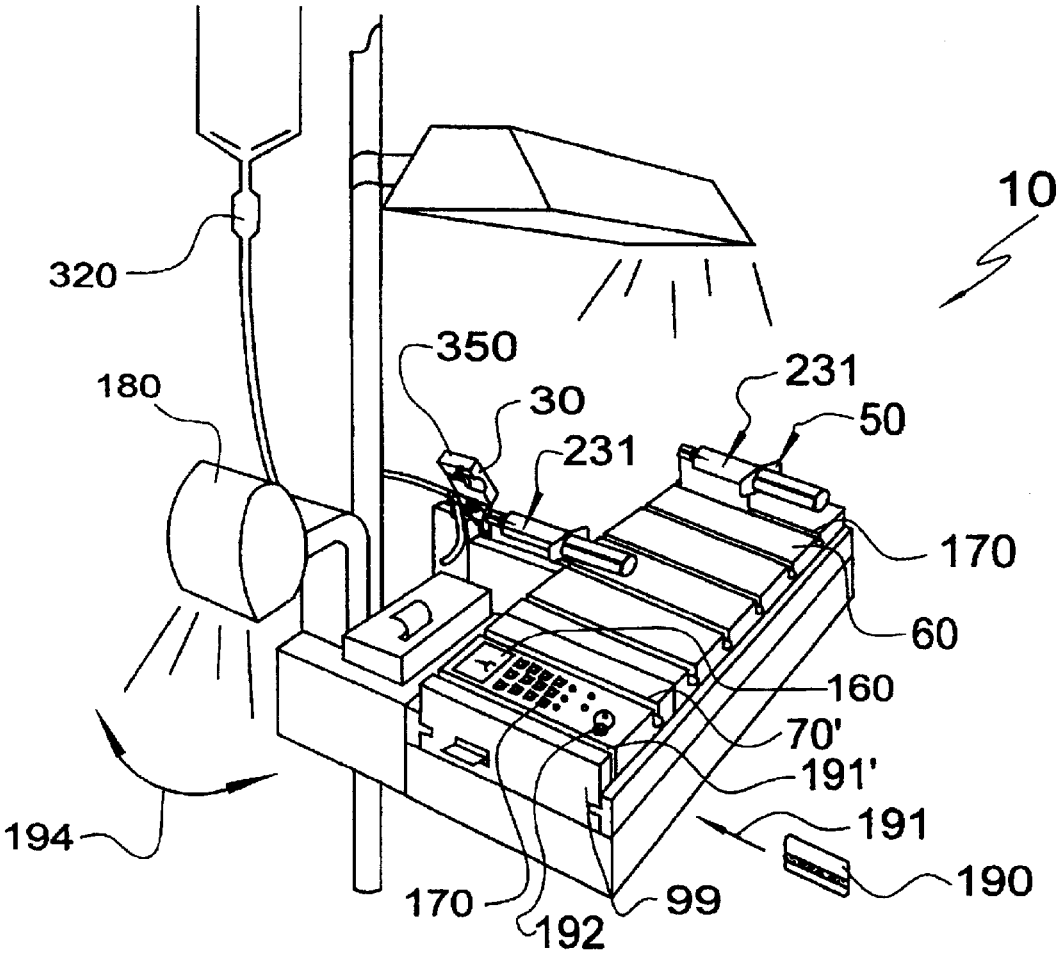
FIG. 2 is a perspective of the medication administration station of FIG. 1 showing a patient data card entry path.

Reference is now made to FIG. 2 wherein a patient card 190 is seen to be entered along a path indicated by arrow 191 through slot 191' whereby data is read for further use by system 10. Access to tray 60 and module 99 is secured by key and keylock 192 disclosed in more detain hereafter. Attention is drawn to double ended arrow 194 which indicates direction and position of movement of indicia to be scanned by optional reader 180.

A key process for using system 10 is preparing a drug or other medical fluid bearing syringe for use. As may be seen in FIG. 3, a syringe 50 is disposed upon a syringe label cradle (SLC) 200 such that a needle 202 of the syringe is juxtaposed and in alignment with port 40. Port 40 is preferably a needless input site to a patient IV set. SLC 200 comprises a label holder, generally designated 204, a needle guard 206 and a slider 208 disposed below label holder 204. Slider 208 is designed to ride in the bottom of a slot 70 and thereby determine the height of SLC 200 (and therefore of syringe 50 relative to port 40.

Figure 3A:
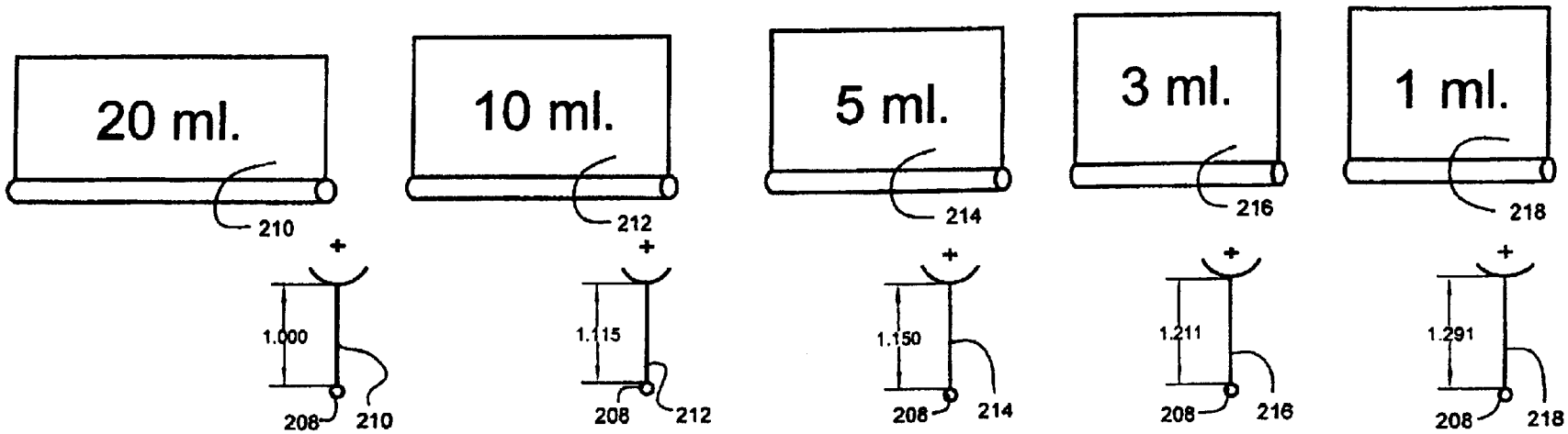
FIG. 3A is a side elevation of label sizes used for a plurality of differently sized syringes, related height dimensions to an injecting needle for each syringe size and relative sizes of label surfaces for the various syringe sizes.

As height of needle 202 is dependent upon the cylindrical diameter of syringe 50 and port 40 is at a fixed height relative to a fixture which holds syringe 50, the height of needle 202 is adjusted by the width of label holder 204. A plurality of needle holders, designated 210, 212, 214, 216 and 218, showing size variances for 20, 10, 5, 3 and 1 ml syringes, respectively are seen in FIG. 3A. Both lateral elevation and end-on views of the needle holders are seen in FIG. 3A. In the end-on view, a constant port 40 height above each slider 208 is indicated by "+" signs.

Figure 3B:
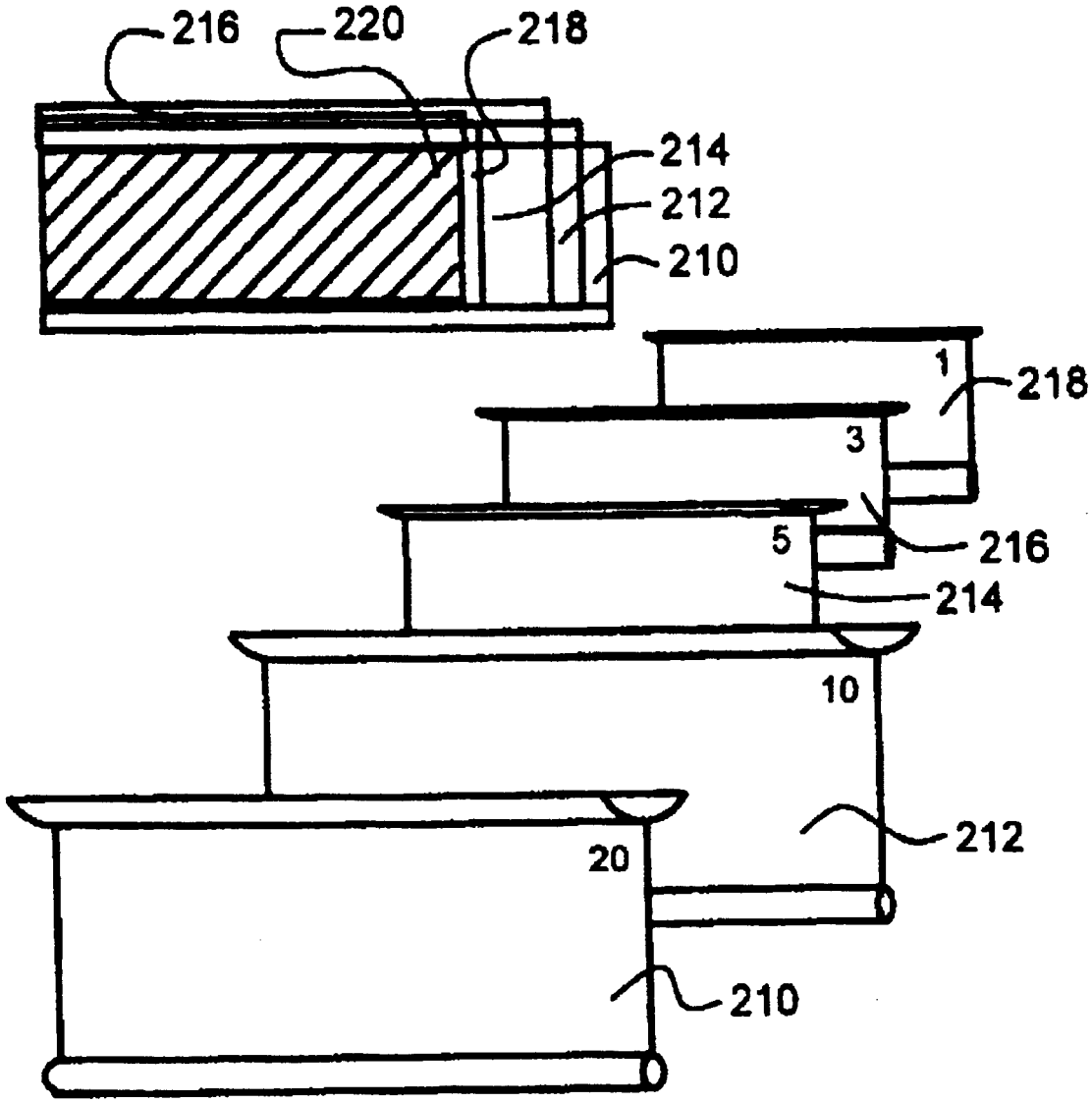
FIG. 3B is a schematic showing representations of overlays of labels seen in FIG. 3A.
Figure 3C:
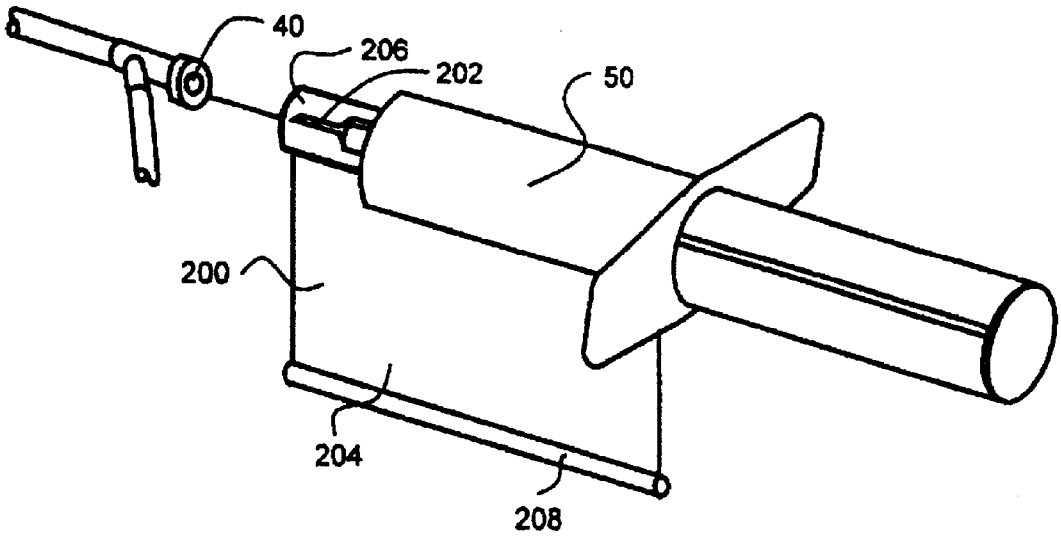
FIG. 3 is a perspective of a syringe disposed in a syringe label cradle (SLC).

It is also desirable to arrange the width of each label holder 204 such that one common label area is available for access by a scanning reader. Such overlap is seen in FIG. 3B. Note that when label holders are juxtaposed, an overlapping area 220 is commonly available for label placement.

Figure 4:
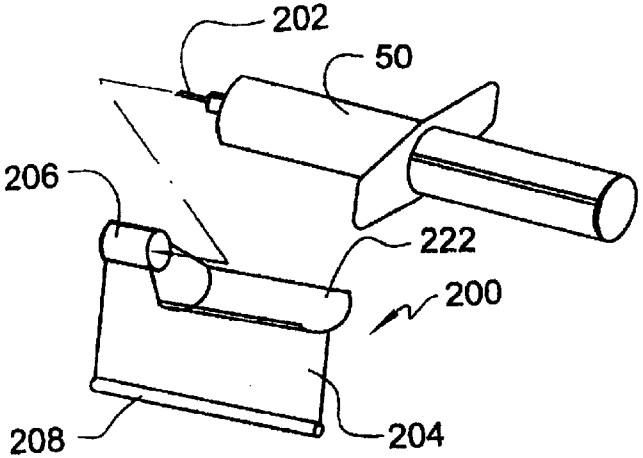
FIG. 4 is a perspective demonstrating a method of placing a syringe onto an SLC and protectively enclosing a syringe needle in a hood.

Reference is now made to FIG. 4 wherein SLC 200 is seen separated from syringe 50. SLC 200 is seen to comprise slider 208, label holder 204, needle guard 206, and a syringe cradle 222. As mentioned earlier, slider 208 is inferiorly disposed to ride in the bottom of a slot 70. The width of label holder 204 determines height of syringe cradle 222 and therefore syringe 50 associated needle 202. Needle guard 206 is disposed to shroud needle 202 when syringe 50 is properly disposed upon SLC 200. To form a syringe/SLC combination, syringe 50 is placed downwardly onto cradle 222 and then slid toward guard 206 until needle 202 is enclosed within guard 206.

Figure 5:
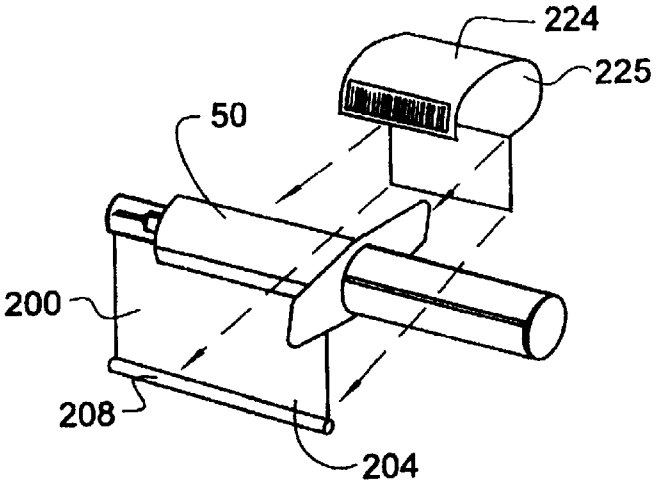
FIG. 5 is a perspective showing label attachment to associated syringe and SLC.
Figure 5A:
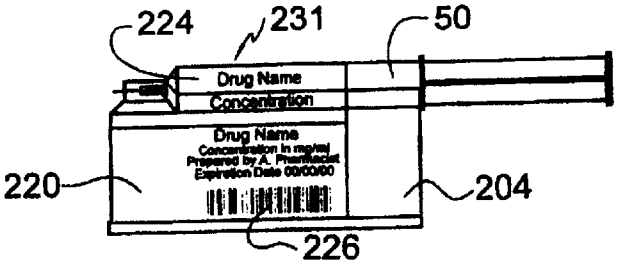
FIG. 5A is a schematic of a syringe and SLC with label attached.

To securely affix syringe 50 to SLC 200, a label 224 is preferably adhesively applied as is best seen in FIG. 5. Generally syringe 50 is affixed to SLC 200 by disposing syringe 50 onto cradle 222. Thereafter, label 224, prepared with an adhesive backing 225, is wrapped about syringe 50 and SLC 200. Label 224 may comprise a wealth of man and machine readable information, but foremost among the information provided thereon are drug name and drug concentration disposed on the visible top of the label for easy viewing by an operator and a bar code 226 (or other machine readable indicia) disposed in the overlapping area 220 where labels are commonly scanned for automatic acquisition of label information. Also, detailed drug information, which may include concentration, preparer, expiration date, expected size of syringe to be used and other pertinent drug delivery information, is commonly printed above the bar code. An example of such label information is seen in FIG. 5A.

Steps commonly used to prepare and initiate a drug infusion and monitoring sequence is seen in FIGS. 6A–D. As described earlier, initial steps include selecting an appropriately sized SLC 200 for a predetermined drug containing syringe 50 and disposing the syringe onto cradle 222 of the SLC 200 by action described by arrow 228 in FIG. 6A. Next, label 224 is preferably affixed to both syringe 50 and SLC 200 by first applying label 224 against the syringe 50 and SLC 200 in direction of arrows 230 as seen in FIG. 6B. Afterward, label 224 is wrapped about syringe 50 and SLC 200 to form an integral unit 231 as seen in FIG. 6C.

Unit 231 is for monitoring during an injection, moved in a fashion described by dashed line and arrow 232 to insert slider 208 of SLC 200 into a slot 70" of a scanner block 234 associated with a patient IV insertion module 30 and in alignment with an injection port 40 as seen schematically in FIG. 6D. In this manner, unit 231 is readied and put in place for drug injection.

Figure 7:
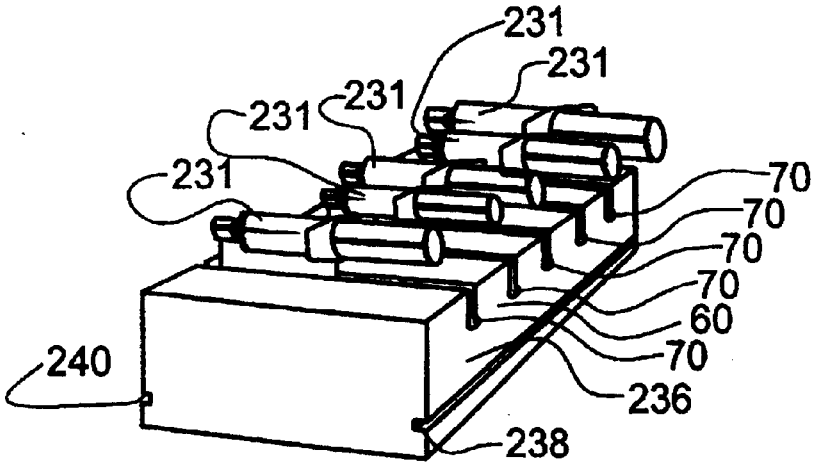
FIG. 7 is a perspective of a plurality of syringes disposed in a cassette tray for transport and use.

Most often, slot 70" of block 234 is also aligned with a slot 70 or 70' of tray 60 which holds a plurality of units 231. Tray 60 is seen in FIG. 7. As seen in FIG. 7, tray 60 accommodates syringes 50 of varied sizes and presents each needle 202 disposed in line with an associated slot 70 and at a constant height for alignment with slot 70" and therefore port 40. Tray 60 comprises a pair of grooves 238 and 240 which are transversely disposed relative to the longitudinal direction of slots 70 and therefore syringes 50 disposed thereon.

Figure 8:
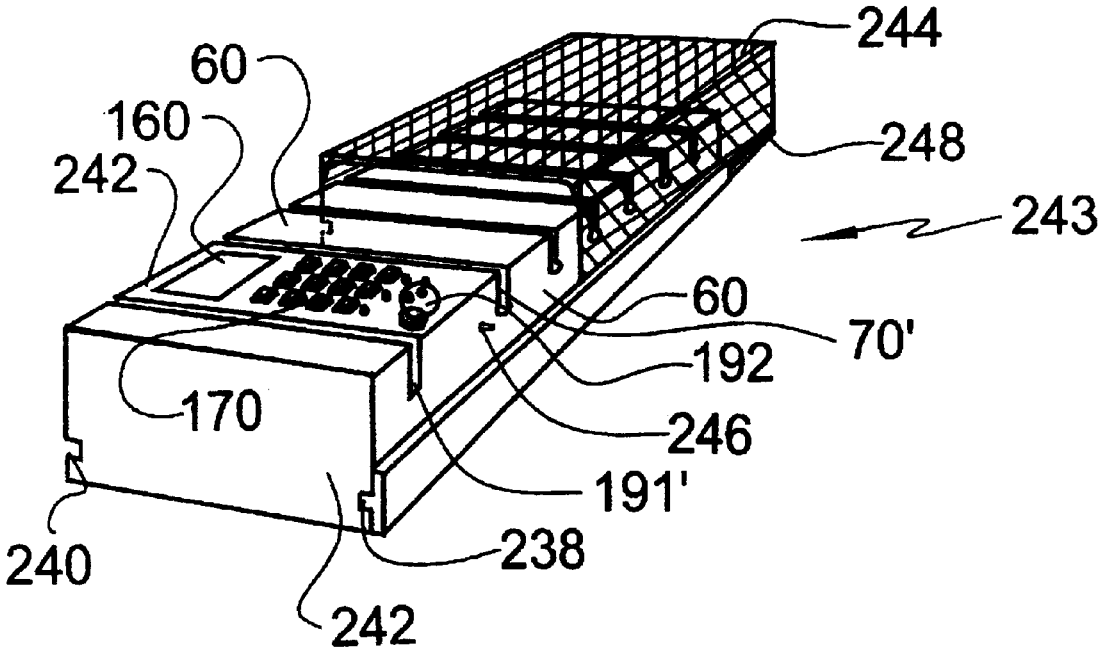
FIG. 8 is a perspective of the tray of FIG. 7 showing addition of a scanner assembly and a lockable cover which slides over the tray to secure the SLC's located therein; addition of the scanner assembly to the tray forms a "smart tray."

Reference is now made to FIG. 8 which shows a scanner module 242 affixed to a tray 60 to form a "smart tray 243." Scanner module 242 is similar in form and function to module 99, earlier described. Scanner module 242 is preferably battery powered and is used for constant monitoring of a controlled substance. Slot 70' is used for intermittent entry and use of syringes which may contain controlled substances. For this reason, slot 70' is generally associated with SLC's which are loaded with syringes at or near a patient site.

For transport, a cover 244 is provided to contain and secure loaded SLC's placed for delivery to a patient site in tray 60. Cover 244 is generally "U" shaped and comprises inwardly bent wings at the open end of the "U" which slide along grooves 238 and 240 to position cover 244 over the loaded SLC's. A lock pin 246, operated by key and keylock 192 is outwardly disposed to pass through a hole (not shown) in a side 248 of cover 244 to securely affix cover 244 to tray 60. Unlocking of by key and keylock 192 withdraws lock pin 246 from the hole in side 248 permitting access to the loaded SLC's. Lock status of pin 246 is detected by an associated microswitch (not shown) located in scanner module 242 to permit electrical monitoring of key and keylock operation. Lock pin 246 is also unlocked automatically under program control of system 10 as disclosed hereafter.

Figure 9:
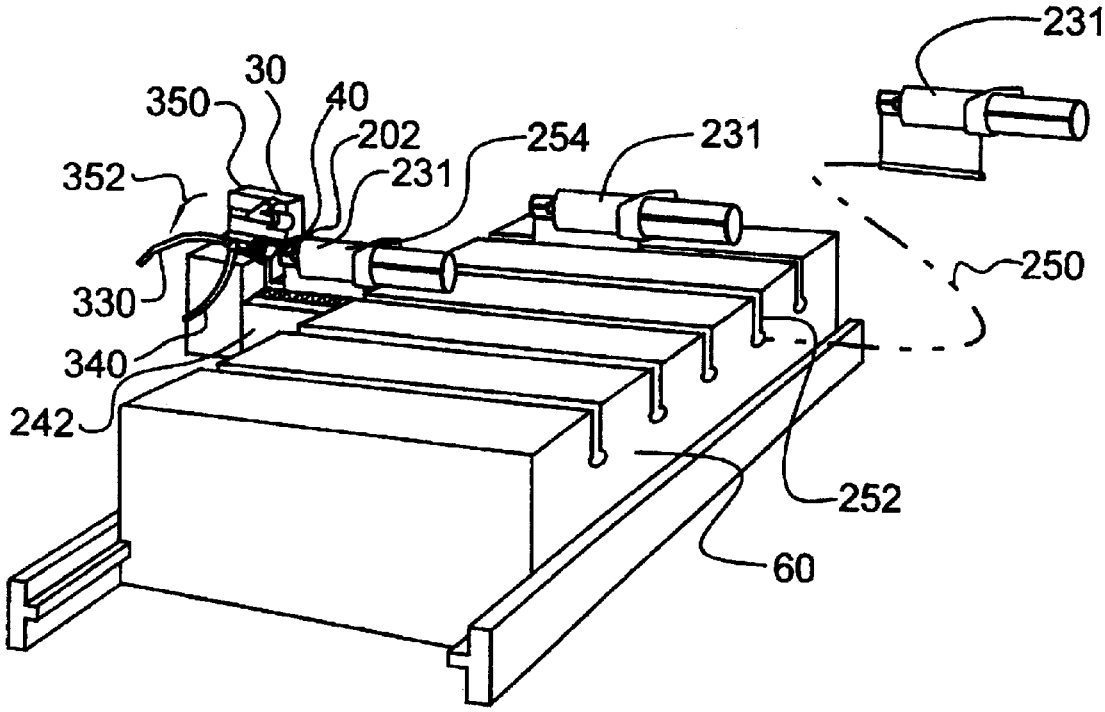
FIG. 9 is a schematic representation of steps related to engaging an SLC and associated syringe into a tray and further into an IV injection port.

A seen in FIG. 9, tray 60 is designed to hold multiple loaded SLC units 231 usually preloaded at a site remote from the patient for later injection. Multiple slots 70 in tray 60 permits used SLC's to be removed and replaced by freshly loaded SLC's with the same or different drugs. An example of loading a fresh SLC unit 231 is indicated by dashed line 250 into a predetermined slot, specially designated 252.

At the time of use of each SLC unit 231, tray 60 is displaced transversely until the needle 202 of selected SLC unit 231 is juxtaposed and aligned with port 40 and slider 208 of SLC unit 231 in its slot 70 is likewise aligned with slot 70". (Slot 70" is best seen in FIG. 6D.) Once selected SLC unit 231, such as SLC unit 254 in FIG. 9, is properly aligned, it is manually displaced to dispose slider 208 in slot 70". Needle 202 is inserted into port 40 and injection is carried out per appropriate medical procedures. Each slider 208 comprises sufficient length (not shown) to interlock slot 70" to slot 70 while the selected SLC unit 231 is disposed in slot 70", thereby restricting movement of tray 60 until the selected SLC unit 231 is returned fully into slot 70. In an emergency tray, 60 may be removed to provide access for drug administration. A plunger scanner, more fully described hereafter, is used to not that a non-SLC associated infusion has taken place.

Figure 12:
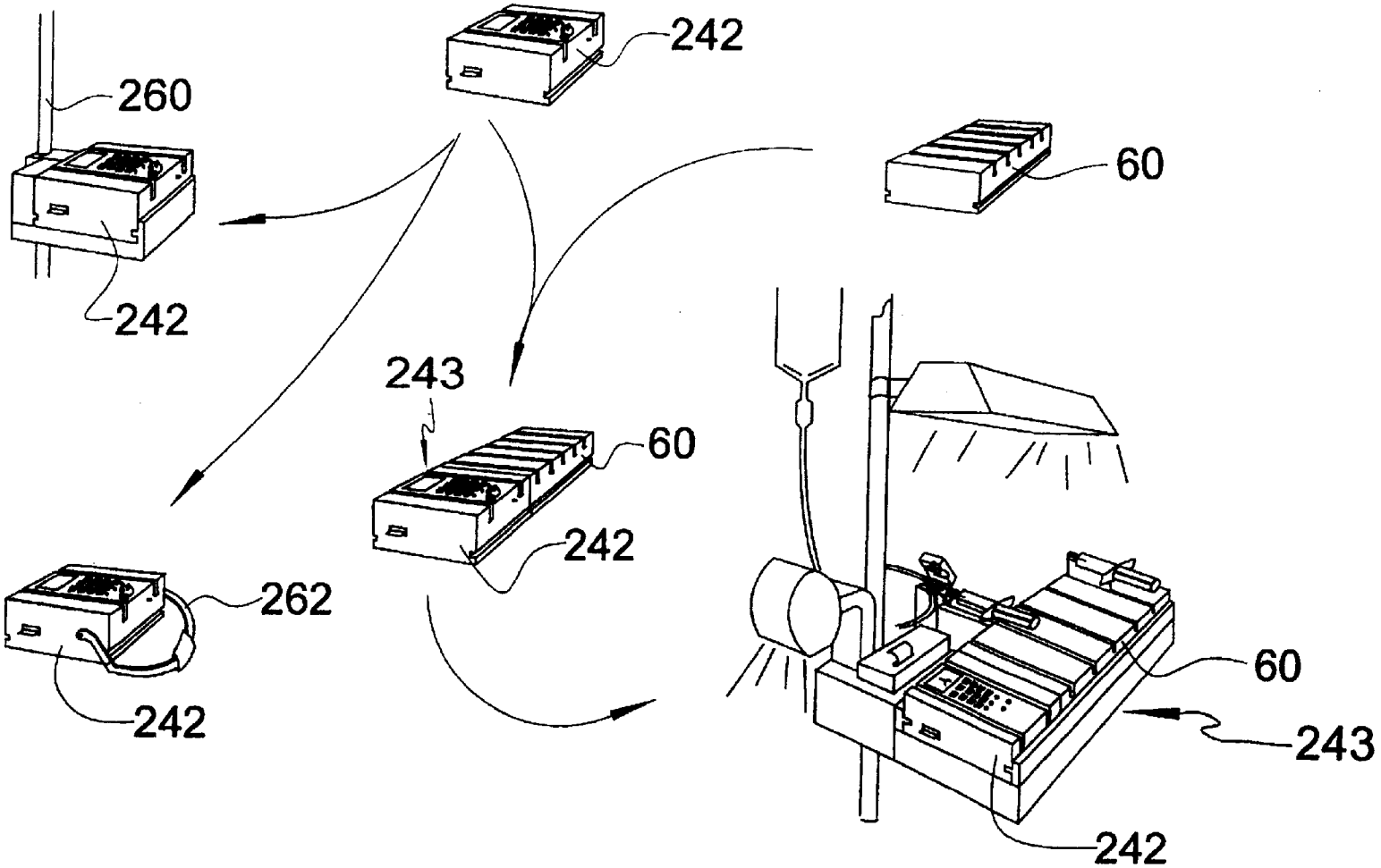
FIG. 12 is a use-flow diagram showing multiple uses of a portable scanner module.

Generally scanner module 242 may be used independently or in conjunction with tray 60 as seen in FIG. 12. Scanner module 242 may be mounted alone on a pole 260 in one form of use. In another form a handle 262 may be attached to scanner module 242 providing a useful portable unit. Also, as earlier described, scanner module 242 may be joined with tray 60 to form a "smart tray 243." Generally, the smart tray is used in conjunction with a complete system 10, as is also seen in FIG. 1.

An important aspect of system operation is detector/reading scanning operation of scanner module 242. As mentioned earlier a label 224 preferably comprising a readable bar code 226 is disposed upon slider 208. In one embodiment, scanner module 242 comprises a pair of scanning devices. A first scanning device 270 comprises an emitter-detector pair and is used to read bar codes as slider 208 is moved into and out of slot 70". Electrical signals from device is transmitted to a microcontroller for processing as described in detail hereafter.

A second scanning device 280 is used to monitor position of a plunger 282 associated with syringe 50 disposed in selected unit 231. Device 280 is seen to be a linear array detector, but other detectors may be used within the scope of the invention. From label 224, information is provided to a system controller 300 (see FIG. 13) relative to syringe size which permits a real-time determination of a volume of fluid delivered or retrieved from a patient as syringe plunger 282 is moved within syringe 50. Ellipse 284 is representative of a lens used to focus an image of plunder 292 on device 280. Such optics and electronic circuits which operate linear array detectors are will known in the art.

Figure 10:
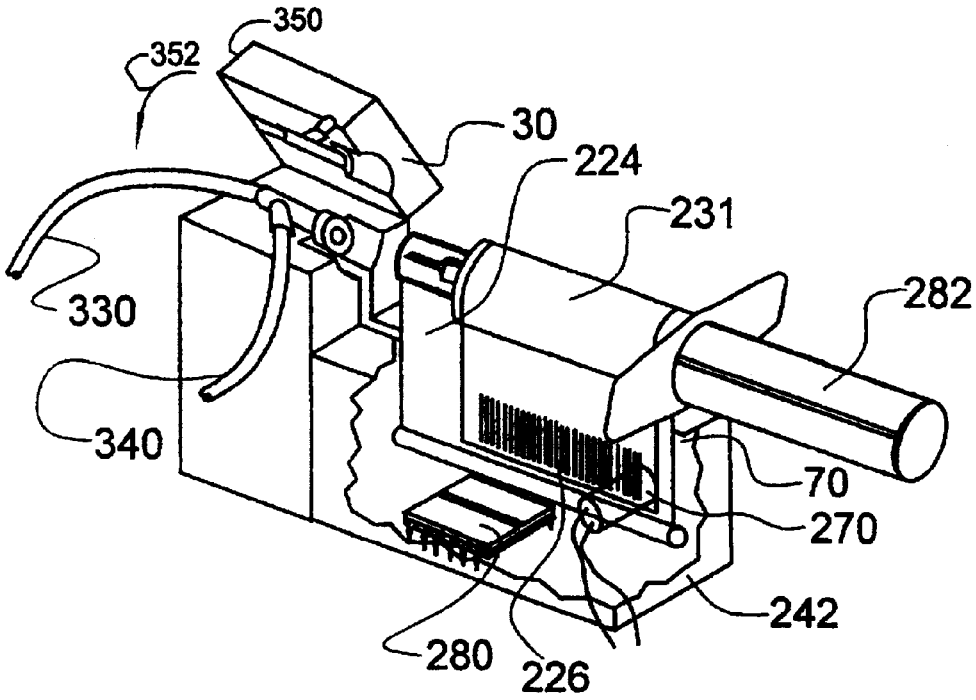
FIG. 10 is a more detailed perspective of the SLC and associated syringe seen in FIG. 9 with parts removed for clarity of presentation.
Figure 11A:
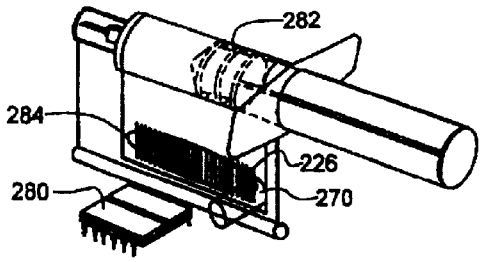
FIGS. 11 A, B, C, D and E are perspective representations of various methods of bar code and plunger displacement scanning of portions of the SLC.
Figure 11B:
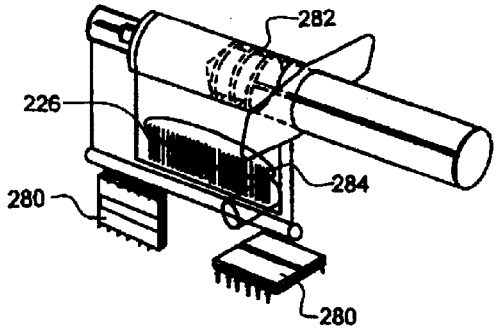
Figure 11C:
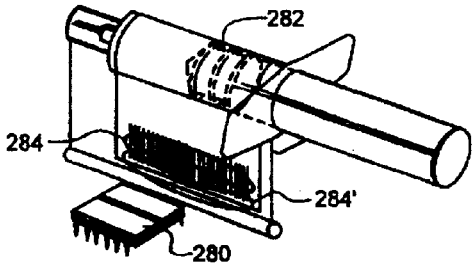

A plurality of scanning devices and device arrangements are seen in FIGS. 11A–E. In FIG. 11A, the configuration seen in FIG. 10 is repeated. In FIG. 11B, a pair of linear array devices 280 are displaced such that a device 280 is used to read bar code 226 while a second device one 280 reads position of plunger 282. In FIG. 11C, a single linear array device 280 is used to scan and determine bar code 226 values and plunger 282 position through a pair of optical lenses 284 and 284'.

Figure 11D:
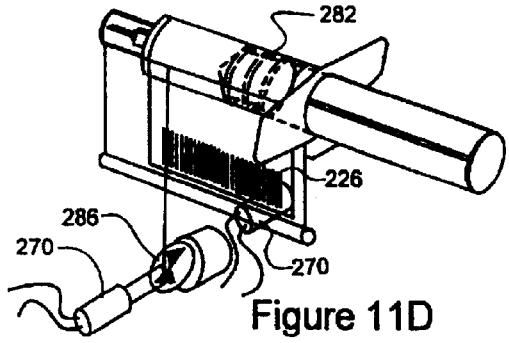
Figure 11E:
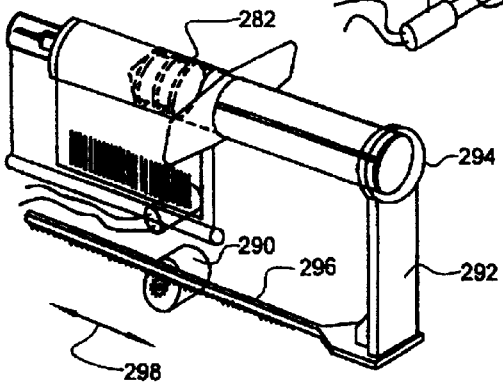

FIG. 11D shows use of two emitter-detector pair devices 270, one of which is used to detect a bar code 226 as seen in FIG. 11A. The other device 270 is used in conjunction with a rotating mirror 286 to scan position of plunger 282. By continuously rotating mirror 286 in direction of arrow 288, and using an angular transducer (not shown) for reference, position and movement of plunger 282 is monitored. Still another bar code scanner and plunger position monitoring configuration is seen in FIG. 11E. Bar code is scanned and read by an emitter-detector pair device 270 as disclosed in FIG. 11A, while plunger 282 position is determined from a linear transducer 290. Such a linear transducer 290 is also readily available in the art. To linearly displace transducer 290, a rigid handle 292 is securely, but releasibly, affixed to plunger 282 on one end 294. Handle 292 is rigidly affixed to an elongated linear arm 296 associated with transducer 290 such that when plunder 282 is moved laterally, arm 296 is likewise laterally moved in the direction of arrows 288. As is well known in the transducer art, such movement is detected by transducer 290 and sent to the system controller.

Figure 13:
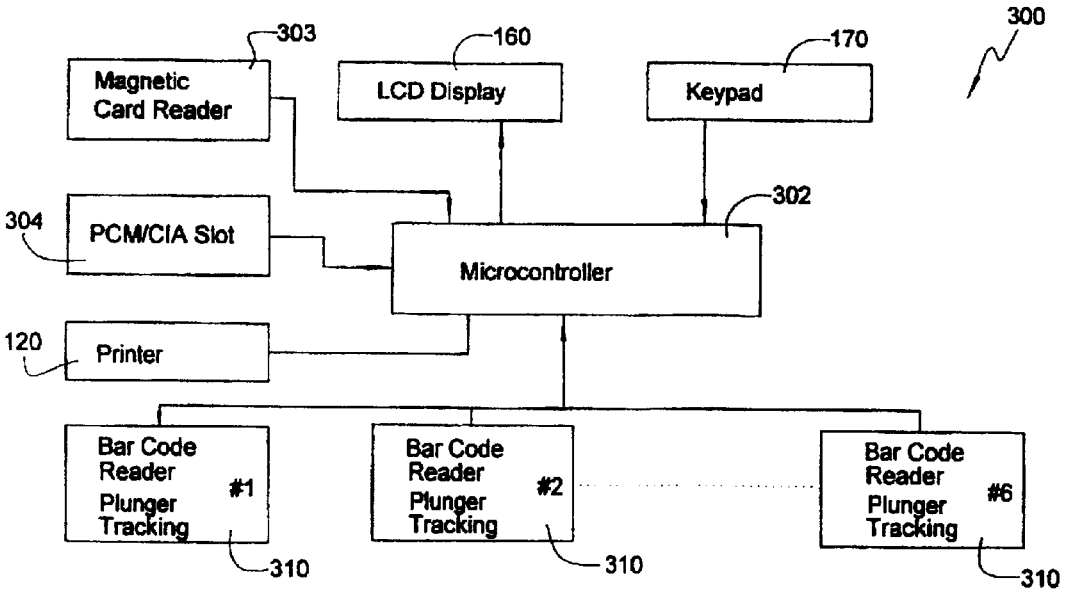
FIG. 13 is a block diagram of the drug monitoring diagram of the instant invention.

A block diagram of an electronic processor 300 for system 10 is seen in FIG. 13. Processor 300 employs parts representing numerous technologies. While there are various parts which may substitute for other parts, review of advantages and disadvantages have resulted in selection of parts recommended for use herein. Even so, some alternatives are disclosed.

Referring to FIG. 13, processor 300 is seen to comprise a central microcontroller 302, keypad 170, LCD (liquid crystal display) 160, a magnetic card reader 303, a PCM/CIA slot 304, printer 120, and a plurality of bar code reader and plunger tracking devices (generally denoted by 310). The bar code reader and plunder tracking devices may be one or more of the configurations seen in FIGS. 11A–E. A more detailed description of function and use of system controller 300 is provided hereafter.

As disclosed above, this novel invention involves control and monitoring of drug delivery in a clinical environment. Drug delivery typically begins at the pharmacy where syringes are preferably pre-loaded with prescribed drugs. Preloaded syringes are then generally delivered to a clinician who administers the drugs.

The first step in the drug loading and preparation process involves matching a selected syringe 50 with an appropriate matching syringe label cradle (SLC). A pharmacist or other qualified profession (generally referenced by PH/QP hereafter) prepares drugs as prescribed. Usually the compliment of delivered drugs are ordered according to a specific procedure (e.g. cardiac, general, orthopedic, etc.) Following is an example of steps which may be involved in preparing a tray 60:

Step 1—The PH/QP notes the size of a selected syringe 50 and selects a matching SLC 200 as disclosed above. Note that it is preferable to color code each SLC 200 for easy identification.

Step 2—Using a bar code imprinting machine, the PH/QP encodes a label 224 with information comprising drug type, syringe size, patient name, identification of the PH/QP, etc. in a format standardized for system 10.

Step 3—The selected syringe 50 is filled with the prescribed drug and places syringe 50 on the matching SLC 200. As part on generally accepted practice, syringe 50 and cradle 200 are preferably placed into a protective hood while syringe 50 is being filled.

Step 4—As necessary, the PH/QP removes adhesive backing from printed label 224 and secures syringe 50 to SLC 200 by wrapping label 224 over syringe 50 and SLC 200 as previously described. Note that label 224 which is disposed across the visible surface of syringe 50 should be made of clear material so that the position of plunger 282 and volume of drug inside syringe 50 may be seen by a using clinician.

Step 5—The prepared SLC unit 231 is then slid into an appropriate slot 70 (docking channel) in a tray 60. Most often, the SLC's are aligned in a sequential pattern such that each next used narcotic is located in the next available docking channel on tray 60 and a reversal agent is located in the last available docking channel. Steps 1 through 5 are repeated for all ordered drugs.

Step 6—Tray 60 is secured by sliding cover 244 into place and extending lock pin 246 to a locked position using key and keylock 192.

Step 7—Transporting tray 60 and its contents to the designated medical procedure site.

An example of steps taken by the tray 60 receiving clinician at the site of the medical procedure is as follows:

Step 1—Tray 60 is slideably loaded onto system 10 using grooves 238 and 240. Access to the drugs is gained by advancing the tray to a predetermined position relative to module 242 whereat entry of an appropriate identification code into the system controller magnetically releases lock pin 246. The identification code my be entered via keyboard 170 or via a magnetic card being swiped through magnetic card reading slot 191'. All such events are stored for recall and audit trail purposes in microcontroller 302.

Step 2—A patient identifying card is placed into PCM/CIA slot 304 304 disposed in system 10.

Step 3—Now active and operable, system 10 provides the following functions:

a. A narcotic syringe is monitored from the time cover 248 is removed, even while in the holding position. It is for this reason that slot 70', being adjacent to module 99 or 242, is dedicated to use by the narcotic syringe.

b. Data obtained from the patient identifying card is automatically read and stored in microcontroller 302. In addition, appropriate hospital data bases and available customized data bases are accessed for information regarding possible allergic reactions, contraindications, drug interactions, etc.).

c. The operator interface comprising the liquid crystal display 160, keypad 170 and printer 120 are activated to provide system status, flash warnings for drug interactions and other pre-programmed instructions to the operating clinician to accept and respond to clinician requests such a request to display chronology of drug administration to the present time.

d. Optical reader 180 is activated for entry of bar code data which should be recorded in the course of the medical procedure.

Referring to FIG. 10, the system 10 utilizes a patient IV system comprising an IV bag and tube set 320 (usually a source of saline), an injection port 40, an associated effluent tube 330 from the set 320 and an influent tube 340 through which fluid is delivered to a patient. A patient IV insertion module 30 is used to contain the confluence of tubes 330 and 340 and port 40. A lid 350 of insertion module 30 is closed in direction of arrow 352 (see FIGS. 9 and 10) to secure port 40 for needle 202 insertions.

Drugs are administered to a patient through port 40 and influent tube 340 by the following steps:

Step 1—Selecting the SLC unit 231 having a desired drug.

Step 2—Relative to orientation of slot 70", transversely sliding tray 60 until slot 70 containing the selected SLC unit 231 is juxtaposed slot 70'.

Step 3—Advancing the selected SLC unit 231 into slot 70", at which time label 224 is read providing drug identification, syringe size/type, preparer and expiration data to microcontroller 302.

Step 4—Immediately thereafter, the current position of SLC unit 231 plunger 282 monitoring begins by activating a light source disposed within module 242, and position and change of position of plunger 282 are detected thereafter automatically.

Step 5—A message on LCD 160 provides verification to the clinician that the SLC unit 231 is properly placed.

Having read bar code data of a so-docked SLC unit 231, microcontroller 302 is programmed to check the name of the drug derived from bar code 226 for a check against possible problems/conflicts. If a problem is determined, an alarm notifies the clinician. A warning message on LCD 160 specifies the nature of the alarm. The problem can be addressed or overridden by the clinician (via keypad 170).

Barring occurrence of difficulties which cannot be readily overcome, system 10 is ready for the clinician to advance plunger 282 to dispense the drug contained in the selected SLC unit 231 at a rate to a volume determined by the clinician. System 10 monitors rate and volume of the injected drug. Once the injection is complete, the selected SLC unit 231 may be returned to a holding position, preferably in its original slot 70.

To complete an injection cycle, the clinician enters acknowledgement of the event into microcontroller 302 via keypad 170. Microcontroller 302 calculates, and stores for future use, residual volumes of drugs unused/remaining in syringes to provide an audit trail comprising notations each last time each SLC unit 231 was scanned while docked in scanning module 242. After final administration of drugs from tray 60, cover 244 is reseated, locked in place and the tray containing all unused drugs is returned to the pharmacy. Unused drugs are disposed of according to protocol.

Referring again to FIG. 13, system controller 300 provides electronic control of system 10, providing basic programmed sequencing of all system functions. At the heart of system controller 300 is microcontroller 302 which comprises a microprocessor, Flash Memory, a Universal Synchronous/Asynchronous Receiver/Transmitter (USART), a Parallel Interface, a Watchdog Timekeeper and a Battery-Backed Static RAM. All of these parts are commercially available.

The microprocessor must be capable of supporting external memory and peripheral devices. There are many microprocessors which are currently available with can perform all system 10 functions adequately. However, an eight or sixteen bit microprocessor with built-in communication hardware for networked applications is preferred. One such microprocessor found to be acceptable is the Intel 8044AH.

It is preferred that Flash memory be utilized to hold the computer operating system. The Flash memory should be configured as a memory mapped peripheral device to the microprocessor. In normal operation, the microprocessor accesses Flash Memory to run the drug monitoring and delivery system programming. In do so, the microprocessor performs diagnostics on system 10 and accesses codes specific to each hospital using system 10. The fact that Flash Memory is erasable and programmable on-line allows system 10 to be custom configured for each user. An additional advantage afforded by using Flash memory is the capability of performing software upgrades via a remote link (e.g. via modem).

The USART, which is part of microcontroller 302, provides a serial interface to printer 120 and keypad 170. Preferably, the USART is memory mapped into the microprocessor's external address space. Writing data to this space loads the USART's communications buffer so that data may be transmitted serially The USART chosen for this application should have two serial ports such that one chip can support both printer 120 and keypad 170.

When the USART receives data from a serial communications device, an interrupt is generated to alert the processor that data is available. The particular chip chosen for this application should be capable of generating an interrupt automatically upon receipt of data. The microprocessor, once interrupted, reads data from the USART's receive buffer. The current Intel USART version is part no. 8251A; the contemporary Motorola USART version is part no. 68681. When choosing a particular chip for this application, care should be taken to assure compatibility with a chosen microprocessor.

The Parallel Interface is used for communications with the PCM/CIA (patient card) slot 304, and LCD 160. The Parallel Interface should be memory mapped into the microprocessors external address space. PCM/CIA slot 304 and LCD 160 should each be assigned a unique address to distinguish between the two. Writing a byte to either of these two addresses thereby sends data to each respective device.

The current Intel version of the parallel interface adaptor chip is part no. 8255A. The Motorola version of the parallel interface adapter part no. 68230. Both Intel's and Motorola's chips provide three independent parallel ports which may be configured individually as either inputs or outputs.

PCM/CIA slot 304, through a parallel port, also provides a modem connection for communications external to system 10. This modem connection may be used for debugging during development of the drug monitoring and for delivery system 10 software via long line (e.g. telephone) communications. The modem connection may also be used for performing remote diagnostics and for installing software upgrades from a remote location.

The Watchdog Timekeeper is a real-time clock and is used as a basis for ensuring that system 10 software is functioning properly. Related real-time clock functions comprise generating interrupts to the processor at a specific time, tracking the usage time of the machine, tracking events, etc. The Watchdog Timekeeper is a critical component of the system since many of the crucial monitoring functions are time based. Any time a time-critical event occurs during the operation of system 10, time of the event must be accurately recorded. The Watchdog Timekeeper is battery backed to maintain an accurate clock. Time from the clock is accessible at any time via keypad 170 and LCD 160.

Timed interrupts are important for interrupting the microprocessor to periodically and regularly test and ensure that system 10 software is functioning properly. For such purposes, the microprocessor receives periodic interrupts from the Watchdog Timekeeper and responds by resetting each interrupt and re-arming the Watchdog Timekeeper to generate another timed interrupt. If system 10 software is not functioning properly, a last generated interrupt is not reset and system 10 operation is halted. Generally, such an event occurs when system 10 computer operation has "gone astray". In this manner, the Watchdog Timekeeper prevents unwanted and perhaps dangerous events from occurring. In addition, the Watchdog Timekeeper generates an alarm when system 10 software is not functioning properly.

There are a number of watchdog type chips, manufactured by Dallas Semiconductor, which may be used-in the system, one of which is Part no. DS1286. The Watchdog Timekeeper is preferably memory mapped into the microprocessor's external address space.

Battery-backed RAM is used to maintain a portion of the data collective by system 10 in a non-volatile state for access after a break in normal power. Making a portion of data of system 10 non-volatile is critically important for this invention since all acquired drug monitoring and delivery drug records are crucial to efficacious medical record keeping. Should a power outage occur in the middle of a procedure, all important data captured and stored by system 10 must be available once power is restored.

Battery-backed RAM is programmed to hold all event data until the end of a procedure, at which time the event data is down-loaded onto the patient data card via slot 304 and made available on hard copy via printer 120. Battery-backed RAM modules may be acquired from Dallas Semiconductor in the form of part no. DS1230Y. Memory size for the microprocessor selected for this application is determined by the expanse of program size required by system 10. Such requirements should be reviewed to provide a basis for selecting a specific memory chip to be used. Preferably, the Battery-backed RAM is memory-mapped into the microprocessor's external address space.

Magnetic card reader 303 provides automatic data input to system 10 and a measure of security. Magnetic card reader 303 is preferred to consist of a standard off-the-shelf magnetic strip reader which may be flush-mounted on a flat surface. Magnetic card reader 303 has a slot through which a magnetically encoded card may be inserted. As an encoded card is passed through the reader slot, encoded data is read and transmitted over a serial port to the microprocessor. Encoded cards contain prerecorded identification of a predetermined clinician planned to use system 10. When initiating system operation, the clinician is prompted to enter an identification code, equivalent to the PIN (personal identification number) used in ATM's (automatic teller machines), through keypad 170. If the identification code corresponds to that stored for the attending clinician as identified on an inserted clinician encoded card, user access to system 10 is permitted and system 10 permits access to drugs in tray 60 and begins monitoring and control of drug delivery. If the identification code does not match the ID, then system 10 sounds an alarm and concurrently denies user access.

Magnetic card reader 303 is optionally used for other purposes including entering drug identification information and drug delivery information. In some embodiments, system 10 is further enhanced to include automatic delivery of drugs using automated plunger 282 actuation mechanisms. In such cases, drug identification and delivery rate is entered by swiping a drug ID card through magnetic card reader 303. Information for each drug is stored in battery-backed RAM or Flash Memory and compared with other stored patient data patient which comprises weight, allergies, etc. In this manner, drug information, including dosage rates, is readily and facilely entered into system 10 permitting drug delivery to be automatically tailored to a patient.

As mentioned earlier, magnetic card reader 303 is connected to the microprocessor through a serial port and USART chip. Communication between the microprocessor and magnetic card reader 303 primarily occurs as data is passed from reader 303 to the microprocessor; however, setup commands may be transmitted from the microprocessor to reader 303 by apparatus and methods well known in the computer art.

Printer 120 is integrated into system 10 for the purpose of producing hard copy of critical system 10 events. Hard copies provide reports of all critical transactions which occur during each operative procedure. Printer 120 is preferably a panel mount, off-the-shelf thermal printer. Communication to printer 120 from the microprocessor is best performed through a serial port, though a parallel port may be used. Preferably, selected printer 120 is capable of printing a line of 40 characters across the width of a printer tape.

The primary function of printer 120 is to provide hard copy record of transactions which occur during an operative procedure. Such a record generally includes time drug is given a drug, the type and amount of drug given. A summary of an entire operative procedure including all drugs administered with total amount administered for each drug is printed at the end of each procedure. In addition, printer 120 is used to report diagnostic information regarding the system during routine inspection and maintenance procedures. A diagnostic software routine, which is readily provided by one who is skilled in computer system programming, detects any failures or errors which occur during operation of system 10. As a consequence of error or failure detection, printer 120 is used to not only print a summary of these errors and failures, but also a list of procedures which should be followed to correct each detected problem. In this manner, output of printer 120 is used to provide self-diagnostics and repair guidance.

Printer 120 is also used to record data gathered for billing purposes should system 10 be leased or rented from a third party. Time that the machine was used under a rental agreement is optionally recorded in batter-backed RAM and supplied as a print-out when the machine is returned or when a billing agent accesses system 10. As an alternative, such information may be downloaded through a modem to a remote billing office.

Keypad 170 is provided to permit user interaction with system 10. Preferably, keypad 170 is a membrane keypad imprinted with custom icons representing action of each key. A keypad decoder converts depression of each key into a ASCII code and then transmits ASCII codes over a serial line which is interfaced to the microprocessor. The keypad decoder is connected to the USART chip which receives the data, stores it, and interrupts the microprocessor. Any time a key is depressed, the microprocessor is interrupted and the microprocessor is programmed to immediately interpret meaning of the interrupt and to take action relative to each key-press.

Custom icons are preferably used to represent each key function rather than using a numbered menu system which might correspond to an LCD 160 displayed menu. Although interaction through the keypad 170 is minimal in a normal procedure, keypad 170 may be used extensively for diagnostic purposes and for performing special functions. For example, a clinician may exercise keyboard 170 to obtain:

1) a summary printout of current status operative procedure before the end of a procedure.
2) status information on system 10 (e.g. how many syringes have been detected by system 10 detected including drug names of drugs read from the SLC units 231).
3) patient information in hard copy.
4) drug interaction information resulting from a comparison of patient information with drug types, etc.

All of this data is readily available through the use of keypad 170. The exact number of keys and their specific functions may vary for each different clinical application of the system.

In a diagnostic mode, keypad 170 is used to instruct system 10 to perform a self-diagnostic procedure and then print results. In this case also, each specific diagnostic routine is preferably identified by a specific graphical icon.

Use of PCM/CIA slots, like PCM/CIA slot 304, is becoming increasingly popular due to their small size and flexibility. A wide range of cards providing a computer connection from modem to memory on a single card not much larger than a credit card made to plug into a standard PCM/CIA slot are presently commercially available. This technology provides a key element for system 10 communications.

System 10 preferably receives patient information through a patient data card (PDC) that plugs into PCM/CIA slot 304. Slot 304 is preferably a PCM/CIA type II slot. This PDC is preferably a battery-backed memory card which receives and stores information regarding a patient scheduled to undergo a system 10 related procedure. Such information is normally derived from a pre-operative interview. Through the use of a PDA (personal digital assistant) patient information entered into a PCM/CIA Type II slot for ultimate use by system 10. Prior to interviewing the patient, a blank memory card is formatted specific to that patient and plugged into the PDA. As information is entered into the PDA, at least a portion of the same information is stored onto the memory card. When the clinician completes the pre-operative interview, the patient card is removed from the PDA and stored for use in system 10. Later, as the clinician prepares the system for use, the memory card specific to that patient is inserted into PCM/CIA slot 304. In due course system 10 reads information regarding the patient from the PCM/CIA slot 304 and makes a logical comparison with drug related information acquired from SLC units 231 assembled onto tray 60.

Upon completion of an given procedure, information regarding drugs monitored by system 10 and amounts available and administered is downloaded to the patient card. The patient card is then removed from the system and forwarded to billing and records for further use by the institution at the site of the procedure. Later, the card may be plugged into another PCM/CIA slot made available on a remote computer and pertinent data downloaded for other uses. Issues related to drug security are facilitated from information made available in this manner to institutional computers.

PCM/CIA slot 304 also allows system 10 to adapt to changes in ways individual hospitals communicate. Eventually, all departments within a hospital are projected to be connected through local area networks with data captured and downloaded to interconnected departments instantaneously. Many institutions have already implemented such networks. The use of PCM/CIA slot 304 on system 10 allows ready adoption to such communication changes. When local area network hardware (e.g., ethernet, token ring) is already available, system 10 can be flexibly incorporated to compatibly become a working part of the hospital network system.

PCM/CIA slot 304 also provides a system a communication link for system 10 through a modem. Through the use of a PCM/CIA formated modem, remote diagnostics are usefully performed on system 10. Should something malfunction on system 10 and a quick fix be needed, remote diagnostics are an important aid to a clinician or technician in evaluating and correcting the malfunction. By plugging a modem card into PCM/CIA slot 304, a remote service facility can dial into system 10 and thereby remotely perform a diagnostic series of tests. If necessary, new software is downloaded to system 10 from the remote site. This is beneficial in maintaining updated software in system 10 with little cost (monetary or system down time) to an end user.

PCM/CIA slot 304 is integrated with the microprocessor through a parallel port. A handshaking scenario, conforming with the PCM/CIA (Type II or Type III standard) is implemented to control the direction of data transfer and timing.

LCD 160 is used to display pertinent information for the clinician regarding the status of system 10 during each procedure. Each clinician is able to determine at all times drugs available in system 10, total amount of drugs delivered to a patient, and drug amounts left in each syringe 50 from LCD 160.

A commercial, off-the-shelf LCD is preferably used in system 10. It is also preferred that LCD 160 have graphical display capability for custom characters and icons generation as well as the enhanced resolution and graphical data presentation. LCD 160 is integrated with the microprocessor through a parallel port and configured as a peripheral to the microprocessor.

Generally during a standard procedure, LCD 160 displays a list comprising names of drugs loaded into the system, amount remaining in each syringe 50 and the current total amount of each drug delivered to a patient. As syringes are changed or additional drugs delivered to the patient, the LCD 160 display is automatically updated. In addition to drug status information, the current date and time is displayed along with certain key patient identification and status data. The exact configuration of the display and all information displayed may be varied by system 10 use and kind and nationality of each clinical site.

In the diagnostic mode, LCD 160 indicates the status of critical subsystems. After a diagnostic routine has been run, LCD 160 is programmably charted to give an indication as to whether each tested subsystem has passed each test or is in need of repair. In addition, LCD 160 lists a series of steps which must be taken to correct an error if one is detected.

Automatic drug identification, syringe 50 size determination and plunger position monitoring are novel elements of the invention. System 10 uniquely monitors drug delivery first by identifying the drug being administered and second by measuring the amount administered in real time by tracking the advancement of syringe plunger 282 as it is moved in syringe 50 to expel liquid into port 40 and onward to a patient.

A plurality of embodiments of plunger 282 tracking devices may be used within the scope of the invention. Further, with some of the embodiments, it is possible to read bar code 226 using the same element which selectively detects plunger 282 movement and position. A plurality of different solid state CCD-based sensors may be used. Line scan array 280 depicted in FIGS. 10, 11A, 11C, and 14 may be employed. A two dimensional array 400 seen in FIG. 15 may also be utilized. Also solid state sensors may be used in conjunction with simple moving parts, such as optically coupled emitter/detector pair 270 which are used in combination with moving parts, such as rotation mirror 286, for example. Another method is use of and transducer 290, mechanically coupled to plunger 282 by an arm 296.

In the case where two line scan CCD elements 280 are used for both reading bar code 226 and position of plunger 282, reliance is placed upon the fact that substantially all syringes are made from a transparent or translucent material and have a high contrast (black) plunger 282 which is easily optically tracked as fluid is delivered through needle 202. In like manner, it is well known that white/black lines in a standard bar code arrangement are also facilely read by like elements and can therefore be used to identify meaning of indicia on label 224.

For desired accuracy, a 1024 pixel CCD sensor is preferred for linear array transducer 280. A four inch lens 284 window running the length of syringe 50 barrel permits transducer 280 a full view of plunger 282 progression. In the reader, it is best to provide a start and a stop band (not shown), imprinted with black ink marks to mark limits of travel of plunger 282. The start and stop bands provide start and stop limits and a measure of a known distance (and therefore syringe 50 volume) therebetween.

In a standard 1024 pixel CCD sensor, pixel sensor elements are evenly distributed over the four inch window. Assuming the width of the start and stop bands to each be one-eighth of an inch in width, each band consumes 32 pixels, leaving 960 pixels available for tracking plunger 282. The tracking length is therefore 3.75 inches. This provides a resolution of 256 pixels/inch or a resolution of 0.0039 inches. If one assumes that there is an error in measurement of three pixels, effective resolution is 0.012 inches.

Volumetric resolution depends upon syringe diameter (i.e. the larger syringe 50, the greater the volumetric error). Effective resolution (Res) may be expressed in terms of syringe 50 radius (r) as:

$$Res=\pi r^2(0.012)in^3$$

The volume of a drug in syringe 50 is calculated using $\pi r^2 l$, where l is the distance from the start mark to needle 202 edge of plunger 282. An incremental volume dispensed as plunger 282 moves from linearly from position $l_1$ to $l_2$ is calculated by:

$$Vol=\pi r^2(l_2-l_1)$$

One who is skilled in the art of drug administration would recognize that measurement accuracy of volumes by measuring plunger 282 position using a 1024 pixel CCD element is adequate. Note that a value for "r" for each syringe 50 is determined from reading label 224.

A preferred method for reading bar code 226 is by a bar code wand which decodes data as SLC unit 231 is advanced into slot 70", eliminating the need to read the entire bar code at one time. An alternative method for reading bar code 226 utilizes a second 1024 pixel linear array 280 as seen in FIGS. 11B and 11C. Using the resolution determining logic and mathematics described above, bar code resolution is also 0.012 inches. For this reason, no black or white line thickness may be greater than 0.012 inches, providing a maximum number of black/white lines of 333. Given an ASCII code in which each alphanumeric character is represented by 8 lines, the largest total number of characters is 41. To conserve drug identification, dates, and identification of a preparing PH/QP, each element is preferably numerically encoded into multiple character equivalents, thereby reducing the total number of characters required by bar code 226.

A light source (not shown in the figures as such light sources are well known in the image detection art) is required to illuminate both syringe 50 and bar code 226. The light source is preferably an array of light emitting diodes (LEDs) placed along side each CCD sensor. The LEDs are strobed individually to expose the CCD elements to selected portions syringe 50 and bar code 226 in a time dependent sequence. See FIG. 11B wherein a pair of linear CCD array sensors 280 are used.

Figure 15:
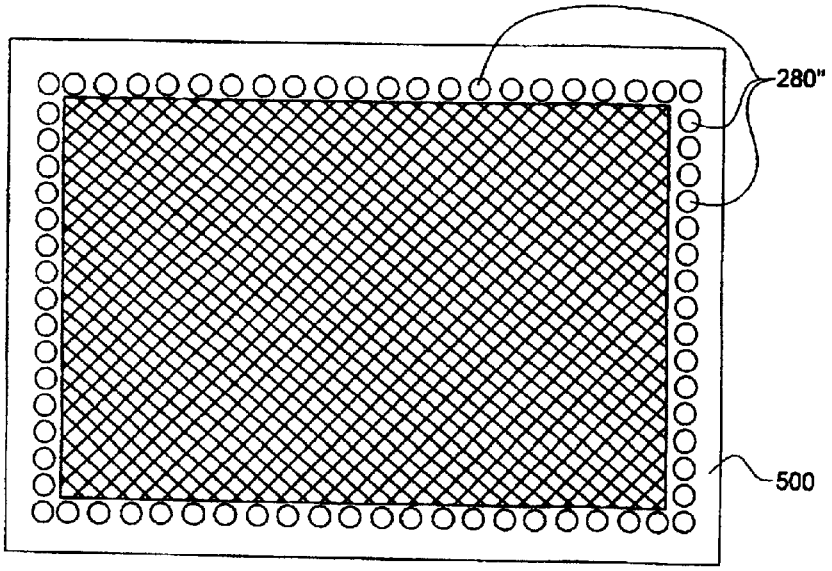
FIG. 15 is a layout of an area scan camera.

An alternative to linear array 280 is the use of a two dimensional area scan CCD such as array 500, seen in FIG. 15. It is preferable to replace linear array 280 with array 500 in single sensor applications, such as the application seen in FIG. 11C. Also, LED array 280' is replaced by LED array 280". This approach uses a single 1024×1024 area scan CCD array 500 to track both plunger 282 and bar code 226. When tracking an area comprising both plunger 282 and bar code 226, the viewing window is about 2 inches in width by four inches in length. As calculated above, length resolution is about 0.012 inches, limiting the number of bar code characters to about 41 as indicated above. However, the width resolution is approximately 0.006, providing sufficient resolution to differentiate between plunger 282 and bar code 226 images with a single element.

The primary difference use of a linear array sensor and an area array sensor in plunger 282 position scanning is that, in tracking plunger 282, a large segment of the 1024×1024 image array may be used to determine the location of plunger 282 and the start and stop bands. Once the bands have been located, microprocessor software need only process those pixels which are along the axis of syringe 50 to locate plunger 282.

Of course, processing the additional data available in a two dimensional array requires a higher speed processor than the lesser amount of data of a linear array requires. One of the advantages, is that a plurality of bar code 226 lines may be detected by an area array, as many as 25 bar code 226 lines for a 1024 pixel width. Such an increase in the number of detectable bar code 226 lines increases the bar code 226 capacity from 41 characters to 1025 characters.

The number of electronic components required to service an area array is much greater than the number of electronic components required to service a linear array. For this reason, unless low cost, very large scale area array decoding chips are available, it is presently economically more reasonable to use linear arrays with the recognized limitations of fewer bar code 282 characters available.

Figure 14:
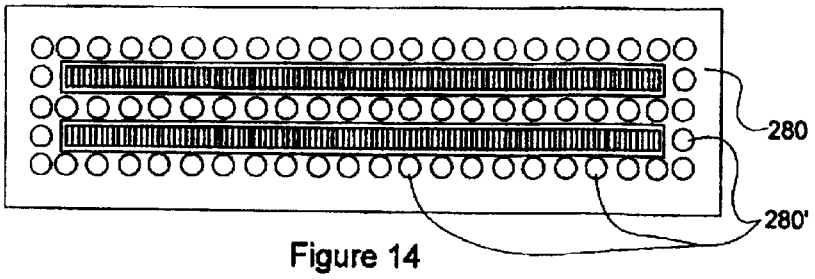
FIG. 14 is an in-line configuration of a pair of line scan cameras.

An array of LEDs is required to illuminate both syringe plunger 282 and bar code 226. A LED array (such a LED array 280') is normally placed around the perimeter of the CCD sensor, as seen in FIG. 14, and is strobed under computer control to illuminate plunger 282 and associated bar code 226. A diagram of the proposed configuration using an area scan CCD is seen in FIG. 11C.

One embodiment of the CCD sensor technology above has been tested using an area scan camera having less resolution that the 1024 element sensor disclosed above. The area scan CCD used in the test comprised 192 horizontal pixels and 164 vertical binary bits. Even the lower resolution was sufficient for adequately tracking a plunger location in a gross fashion. In this case, resolution was inadequate for tracking the plunger in only the smallest syringe (5 cc).

For the test, a mock-up base tray was constructed and six syringe sizes were prepared with a bar code 226 printed on a clear acetate label 224. Acetate label 224 was formed around syringe 50 such that a small rectangular section protruded away from the syringe. This rectangular section was used to hold bar code 226 (which was printed on the side and partially on the bottom) and to secure syringe 50 to a base tray (function of SLC 200). The center of the rectangular protrusion was clear so that plunger 282 could be visibly accessed through label 224. The distance from the bottom of acetate label 224 to syringe plunger 282 varied depending on the size of plunger 282 (the distance being greater for smaller syringes). The CCD array was located on the under side of the base tray along with an LED array for illumination. This embodiment permitted tracking plungers of selected sizes of syringes using the 192×164 CCD sensor.

Figure 16:
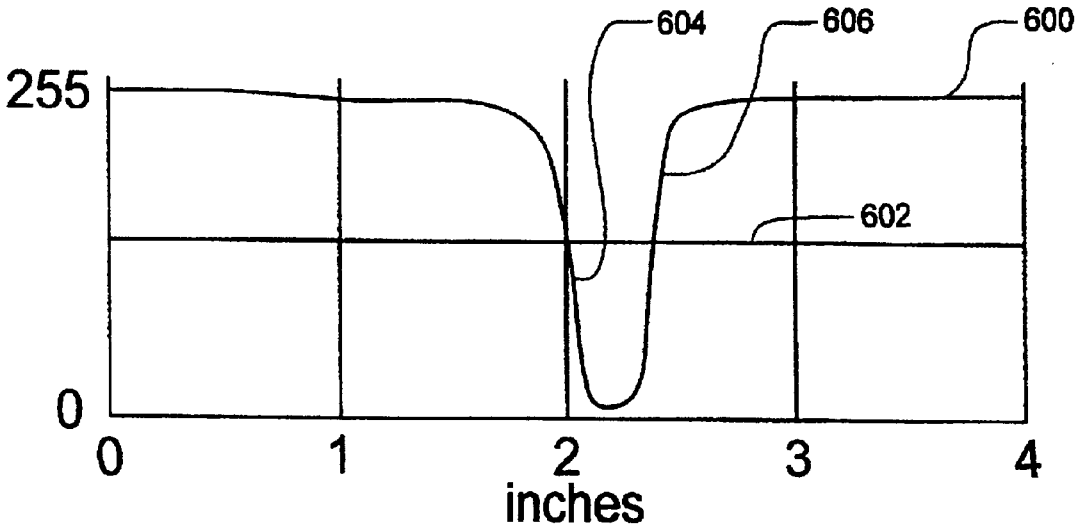
FIG. 16 is a graphical representation of a syringe plunger position located by measured output of a scanning camera.

FIG. 16 illustrates a typical curve 600 obtained when sensing location of syringe plunger 282. Note that curve 600 is a graph of measured light intensity (sensor output) versus barrel length of syringe 50. Note also that a critical level for sensing each side of barrel image is denoted by a threshold level 602. A system software program permits one to identify a white to black transition of plunger 282. A calibration image taken of the syringe permitted a path to be calculated from the tip of syringe 50 to the distal end of its cylindrical barrel. This path provided definition of where software was to track to detect white to dark transition. White was defined as having a digital binary sensor output value of 255 while black was defined as having a digital binary sensor output value of 0. The graph in FIG. 16 illustrates the transition from light (white) to dark (black) as sensed by the CCD sensor when processing an image along a path running parallel to and in the center of syringe 50 barrel. A sharp dip 604 seen in graph 600 identifies the beginning of the plunger, the trough associated with dip 604 is indicative of the width of plunger 282. A sharp rise 606 identifies the back or end of plunger 282. As plunger 282 was advanced, the graphic profile of line 600 clearly and relatively accurately described the position of plunger 282. It is evident to one who is skilled in the signal processing art that such a signal can be used to accurately determine position and movement of plunger 282.

The process was repeated for a plurality of varied sizes of syringes 50. The CCD sensor was able to adequately locate plunger 282 for all syringes except the smallest (size 5 cc). It was determined that failure to read the plunger position of the small syringe was due to the fact that the small syringe was located the greatest distance from the base tray and acetate label 224 was not truly clear. The black plunger was indistinguishable on the smallest syringe because of reduced resolution due to lack of acetate clarity and distance of syringe barrel from the reader.

Even so, this testing with a reduced resolution reader clearly proved the feasibility of using an optical system for tracking progression of a plunger. As sensitivity of a sensor system is increased, resolution becomes greater and accuracy in tracking a plunger and calculating drug volume and volumetric changes is improved. It should be readily apparent to one skilled in the visual sensor art that plunger movement of even the smallest cylinder used in the test is detectable with improved sensor resolution.

An alternative technology which may be used to both read the bar code and track the syringe plunger is an infrared emitter/detector pair 270 (see FIG. 11D), mechanically scanned over an area of interest. The emitter directs an infrared beam onto a surface and the detector receives reflected light. Successful operation of this concept is based upon the fact the black objects absorb more light than white surfaces making, the difference between black and white discernable.

To mechanize emitter/detector pair 270, a mechanical actuator consisting of an electric motor with a cam is attached to a shaft. A beam splitter/mirror 286 is attached to the cam such that the emitter's infrared beam is scanned across the area of interest. Beam splitter 286 allows infrared light from the emitter to be directed outward toward the surface of interest and causes reflected light to pass through to the detector. The detector responds to the reflected light by outputting a voltage which is proportional to the intensity of sensed reflected light. By setting a threshold between the intensity received from a light surface and the intensity received from a dark surface, a binary output can be determined which indicates whether the surface is white or black. As beam splitter/mirror 286 is rotated in direction of arrow 288 by the electric motor, the entire surface of interest is scanned. Speed at which the motor is rotated and the sampling rate of signals from pair 270, in combination, determine the resolution of this detector system. This proposed concept is illustrated in FIG. 11D.

When reading bar code 226, each scanner works in a manner which is similar to scanners seen in a grocery store. A beam is scanned across bar code 226 to distinguish between light and dark stripes. If a starting location is either predetermined or known through an indicator encoded within bar code 226, the microcontroller begins reading bar code 226 to distinguish between light and dark stripes. If a starting location is either predetermined or known through an indicator encoded within the bar code, the microcontroller begins reading bar code 226 by counting the number of white and black stripes.

Reading the location of the syringe plunger may be more difficult using the emitter/detector pair 270 but extensions of the methods disclosed above permit determination of plunger 282 position. Since the infrared beam is scanned over the entire area of interest (syringe 50 and bottom of the slider 208), the reflected beam is sampled sufficiently fast to create a black/white image of the area. From this image, start and stop marks on syringe 50 are located as well as the black image of the syringe plunger 282.

An advantage of this approach is the relatively inexpensive technology required to implement an emitter/detector pair 270. From an economical standpoint, this approach appears to be the best compared to other sensor approaches described heretofore. However, there are some drawbacks to the emitter/detector pair 270 which cause this embodiment not to be currently preferred. First, use of a mechanical actuator introduces a weak point in system 10 from the standpoint of ruggedness. System 10 must endure rugged manipulation by a user, including being knocked over or dropped. Further, a mechanical actuator must be precisely calibrated to scan an area of interest to make sure that a beam splitter/mirror 286 combination is aligned with emitter/detector pair 270. The likelihood of failure of a solid state CCD-based system is much less, making embodiments seen in FIGS. 11A–C preferable.

Computer processing time required to sample a syringe plunger 282 position and bar code 226 information by the embodiment of FIG. 11D is greater than time required to read a CCD sensor, especially if a linear CCD (as seen in FIG. 11B) is used. Finally, economics presently dictate that a single emitter/detector subsystem be used to scan all syringes, making the time required to scan all syringes by the embodiment of FIG. 11D, much greater than the scanning time of a multiple CCD based system. Note that there is a potential for an event to be missed or a system response delay due to the time required to scan and sample each syringe with one emitter/detector sensor. This is further cause for selecting the multiple CCD-based system over the emitter/detector pair.

Another approach to plunger 282 tracking and bar code 226 reading utilizes a mechanical method of tracking plunger movement and reading a bar code as seen in FIG. 11E. This method is the easiest to implement; however, it is the most cumbersome for a clinician to set up and use. Because of clinician (user) difficulties in using this approach, it is not presently preferred.

Mechanical reading of bar code 226 may be performed by using an off-the-shelf bar code wand which is integrated into the system. Before SLC unit 231 is slid into base tray 60, a clinician runs the bar code wand over bar code 226. Data encoded on the bar code is read and decoded by system 10. One major disadvantage of this approach is a requirement for the clinician to perform a scanning step without a guarantee that SLC unit 231 will thereafter be placed into a correct slot.

Mechanical tracking of plunger 282 movement is accomplished by using an alternative holder which includes arm 296 that extends back to the portion of a plunger which is disposed at a site where a clinician pushes. A schematic representation of this holder is provided in FIG. 11E. As the clinician advances plunger 282, the extending arm is also advanced. Since the extending arm 296 runs underneath the syringe and is exposed underneath the holder, mechanical roller 290 with an attached encoder may be used to track progress. An incremental encoder attached to the shaft of a free-wheeling roller tracks progress of the plunger as the clinician advances it. Resolution of this system depends on resolution of the incremental encoder, generally expressed in counts/revolution. Encoders having adequate resolution are readily commercially available. In addition, the track in which the extension arm 296 rides may be grooved such that retracting the plunger 282 is prohibited as long as syringe 50 remains in the system 10. The method used to prohibit plunger 282 retraction may make use of insertable plastic parts which operate in a manner similar to catches used in making wire ties.

The main advantage to using a mechanical method for tracking plunger 282 is the relative low cost of implementing the mechanical technology. Fabricating a roller with incremental encoders is the most easily achieved of all alternatives thus far described. Such implementation allows the system computer to track each syringe simultaneously and any movement is immediately detected. However, as mentioned earlier, a major disadvantage is found in the mechanical aspects of the system.

Notably, an additional advantage is the inclusion of mechanical extension arm 296 which provides a basis for automatically advancing plunger 282 without manual assistance. Attachment of an electric motor to advance plunger 282 in response to a clinician's direction is well within the current state of the art for automated medical systems. Using such plunger 282 advancement, a clinician would enter the drug and amount to be delivered to the patient into the system 10 through keypad 170. System 10 then determines which slot the desired drug is located in and automatically advances each plunger 282 at a programmed rate until the desired drug volume has been delivered. When contemplating automatic delivery of drugs, obvious legal issues must be addressed; however, automatic drug delivery is now in use in hospitals and system use is generally accepted.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A drug delivery and monitoring system comprising: a drug delivery station comprising:

an interface to a patient IV set comprising a port exposer for exposing a port of the IV set for medical needle insertion and a needle aligner for aligning the needle at the port;

a syringe label cradle (SLC) unit comprising:

a medical syringe comprising an elongated barrel having a known transverse diameter and a medical needle disposed along the longitudinal axis of the barrel;

a SLC comprising a cradle for the syringe and a slider which is disposed to slideably ride within said needle aligner to deliver the medical needle to a port in a patient IV set and which comprises an area for a bar code label and a vertical slider width which adjusts the needle to a predetermined height relative to the port; and a label which is securely affixed to the medical syringe, the label comprising patient correlation indicia which is readable by a label indicia reader;

an SLC unit delivery tray which provides secure containment for one or more SLC units including the aforesaid SLC;

a microprocessor controller;

the drug delivery station further comprising:

a syringe plunger position determining sensor whereby the system measures the plunger position and change of position as a drug is delivered to the patient; and the aforesaid label indicia reader for automatically reading critical drug identification information from the label.

2. A drug delivery and monitoring system according to claim 1 wherein the interface comprises a needleless injection site.

3. A drug delivery and monitoring system according to claim 1 wherein said drug is delivered manually.

4. A drug delivery and monitoring system according to claim 1 wherein the needle aligner comprises a slot for the slider.

5. A drug delivery and monitoring system according to claim 1 wherein the syringe has a known barrel diameter and the SLC is selected to conform with the barrel diameter of the syringe.

6. A drug delivery and monitoring system according to claim 1 wherein said label comprises machine readable bar code indicia.

7. A drug delivery and monitoring system according to claim 6 wherein said bar code indicia comprises a drug identifier, an expiration date of the drug and a preparer of the drug.

8. A drug delivery and monitoring system according to claim 1 wherein the slider comprises space for a bar code at a predetermined location on the slider.

9. A drug delivery and monitoring system according to claim 1 wherein the label is made from optically clear material.

10. A drug delivery and monitoring system according to claim 9 wherein the optically clear material is acetate.

11. A drug delivery and monitoring system according to claim 1 wherein the label comprises man-readable indicia disposed at a conveniently viewable site on the SLC unit.

12. A drug delivery and monitoring system according to claim 1 wherein said containment comprises a lockable cover.

13. A drug delivery and monitoring system according to claim 12 wherein said microprocessor comprises controls for unlocking the cover.

14. A drug delivery and monitoring system according to claim 1 wherein said controller comprises a keypad.

15. A drug delivery and monitoring system according to claim 1 wherein said controller comprises a display.

16. A drug delivery and monitoring system according to claim 15 wherein said display is a liquid crystal display (LCD).

17. A drug delivery and monitoring system according to claim 1 wherein said controller comprises battery backed memory whereby data is retained through power failure.

18. A drug delivery and monitoring system according to claim 1 wherein said syringe comprises start and stop marks which provide calibrating limits for the position determining sensor.

19. A drug delivery and monitoring system according to claim 1 wherein the sensor comprises at least one linear CCD array.

20. A drug delivery and monitoring system according to claim 1 wherein the sensor comprises at least one emitter/detector pair.

21. A drug delivery and monitoring system according to claim 1 wherein the sensor comprises at least one area scan CCD array.

22. A system according to claim 1 wherein the label comprises adhesive backing by which it is placed and held in its position.

23. A system according to claim 1 wherein the label indicia reader comprises an output site by which the patient is correlated to the drug.

24. A system according to claim 1 wherein the sensor comprises an output site by which the quantity of the drug administered is correlated to the patient.

25. A drug delivery station comprising:

an interface to a patient IV set comprising a port exposer for exposing a port of the IV set for medical needle insertion and a needle aligner for aligning the medical needle at the port;

a syringe label cradle (SLC) unit comprising:

a medical syringe cradle, a space for a label and a slider which in combination with a syringe comprising a needle, a barrel, and a plunger and position of the cradle relative to the slider provides vertical alignment for the needle such that the syringe needle is juxtaposed the interface when the SLC unit is disposed in the needle aligner;

a label securely affixed to the syringe and which comprises machine readable drug identifying indicia;

a label indicia reader for automatically reading drug identification information from the label;

a syringe plunger position determining sensor whereby the station measures the plunger position and change of position as a drug is delivered to the patient from the medical syringe;

the barrel having a known transverse diameter with the medical needle disposed along the longitudinal axis of the barrel;

the slider being disposed to slideably ride within said needle aligner to deliver the medical needle to the port, the SLC comprises an area for the bar code label and the slider comprising a width which adjusts the needle to a predetermined height relative to the port.

26. A drug delivery and monitoring system according to claim 25 wherein said syringe comprises start and stop marks which provide calibrating limits for the position determining sensor.

27. A drug delivery and monitoring system according to claim 25 wherein the sensor comprises at least one linear CCD array.

28. A drug delivery and monitoring system according to claim 25 wherein the sensor comprises at least one emitter/detector pair.

29. A drug delivery and monitoring system according to claim 25 wherein the sensor comprises at least one area scan CCD array.

30. A syringe label cradle (SLC) unit comprising:

a medical syringe comprising an elongated barrel having a known transverse diameter and a medical needle disposed along the longitudinal axis of the barrel;

a SLC comprising a cradle for the syringe and a slider which is slideably disposed at the SLC to deliver the medical needle to a port in a patient IV set, the SLC further comprising an area for a bar code label, the slider comprising a vertical width which adjusts the needle to a predetermined height; and a label which is carried by the SLC, the medical syringe being securely affixed to the SLC, and the label comprising indicia which is automatically readable by a label indicia reader.

31. A smart tray for holding and selectively delivering a plurality of syringe label cradle (SLC) units to a drug delivery and monitoring system, said smart tray comprising:

a first SLC unit tray portion comprising a transverse width which is at least as wide as the longest SLC unit which it holds and a length consistent with receiving and holding said plurality of SLC units;

a plurality of slots disposed transversely relative to said length, each slot having a depth which is the same as the other slots;

a second portion of the smart tray which is releasibly affixable to the first portion, said second portion comprising:

a data entry mechanism for entering patient data;

a control panel comprising:

a computer output display;

an input keypad;

a slot for one SLC unit wherein the SLC unit is constantly monitored;

a lockable cover which securely releasibly affixes the SLC units to the smart tray.

32. A method for delivering and monitoring drugs to a port in an IV set comprising the steps of:

delivering a [safety] *syringe* label cradle unit to the port such that a needle on a drug loaded syringe which is a part of the [safety] *syringe* label cradle unit is inserted into the port;

automatically determining identification information relative to the drug contained in the syringe by electronically scanning a label on the [safety] *syringe* label cradle unit;

pushing a plunger of the syringe to deliver a volume of the drug through the port;

monitoring movement of the plunger for the purpose of calculating and storing the volume of drug delivered.

*33. A method for delivering and monitoring drugs to a port in an IV set, said method comprising delivering a needle on a drug loaded syringe to the port, automatically determining identification information relative to the drug contained in the syringe by electronically scanning a label associated with the syringe, inserting the needle into the port, pushing a plunger of the syringe to deliver a volume of the drug through the port, and monitoring movement of the plunger while delivering the drug for calculating the volume of the drug derived from the syringe.*

*34. The method of claim 33, wherein the label is adhered to the syringe.*

*35. The method of claim 33, further including providing a cradle for the syringe.*

*36. The method of claim 35, wherein the label is adhered to at least a portion of the cradle.*

*37. The method of claim 33, further including storing information relative to the volume of the drug derived from the syringe.*

*38. The method of claim 37, further including storing information relative to the identification of the drug being delivered.*

*39. The method of claim 33, wherein monitoring movement of the plunger comprising optically sensing the movement of a portion of the plunger in real time using an optical sensor.*

*40. The method of claim 39, wherein said optical sensor comprises at least one linear CCD array.*

*41. The method of claim 39, wherein said optical sensor comprises at least one area scan CCD array.*

*42. The method of claim 39, wherein said optical sensor comprises at least one optical emitting/detector pair.*

*43. A method for delivering and monitoring drugs to a port in an IV set comprising the steps of delivering a needle on a drug loaded syringe into the port; automatically determining identification information relative to the drug contained in the syringe by electronically scanning a label; pushing a plunger of the syringe to deliver a volume of the drug through the port; monitoring movement of the plunger for the purpose of calculating and storing the volume of drug delivered.*

*44. A syringe label cradle unit comprising a medical syringe comprising an elongated barrel having a needle extending therefrom, said needle having an end attached to said barrel and another end remote therefrom, cradle means for supporting said syringe having a holder for adhering a label containing machine readable information, said another end of said needle being accessible when said syringe is supported by said cradle means.*

*45. The unit of claim 44, wherein said information comprises information regarding the identification of a drug to be delivered by said syringe.*

*46. The unit of claim 44, wherein said information is in the form of a bar code.*

*47. The unit of claim 44, wherein said cradle means includes a needle guard for said needle.*

*48. The unit of claim 44, further including a label securing said syringe to said cradle means, wherein said information comprises information regarding the identification of a drug to be delivered by said syringe.*

*49. A drug delivery system comprising an interface to a patient IV set including a port exposer for exposing a port of the IV set for needle insertion, a syringe comprising an elongated barrel having a needle extending therefrom, a label in association with said syringe containing machine readable information regarding the identification of a drug to be delivered by said syringe, a label indicia reader for reading said information on said label, and a syringe plunger position determining sensor, said sensor determining changes of the plunger position as a drug is delivered from said syringe, the plunger movement being determinative of the volume of the drug delivered from said syringe.*

*50. The system of claim 49, wherein said label is adhered to said syringe.*

*51. The system of claim 49, further including a cradle for said syringe.*

*52. The system of claim 51, wherein said cradle includes a holder to which said label is adhered.*

*53. The system of claim 49, wherein said sensor comprises an optical sensor.*

*54. The system of claim 53, wherein said optical sensor comprises at least one linear CCD array.*

*55. The system of claim 53, wherein said optical sensor comprises at least one area scan CCD array.*

*56. The system of claim 53, wherein said optical sensor comprises at least one emitting/detector pair.*

*57. The system of claim 49, wherein said information is in the form of a bar code.*

* * * * *